(12) United States Patent
Rouits et al.

(10) Patent No.: US 12,144,818 B2
(45) Date of Patent: Nov. 19, 2024

(54) METHOD FOR TREATING CANCER IN A HUMAN PATIENT BY ADMINISTERING AN ANTI-CD37 IMMUNOCONJUGATE USING VARIOUS DOSING REGIMENS

(71) Applicant: DEBIOPHARM INTERNATIONAL, S.A., Lausanne (CH)

(72) Inventors: Elisabeth Rouits, Crissier (CH); Nigel Mccracken, Begnins (CH)

(73) Assignee: DEBIOPHARM INTERNATIONAL, S.A., Lausanne (CH)

(*) Notice: Subject to any disclaimer, the term of this patent is extended or adjusted under 35 U.S.C. 154(b) by 979 days.

(21) Appl. No.: 17/059,698

(22) PCT Filed: May 29, 2019

(86) PCT No.: PCT/IB2019/054457
§ 371 (c)(1),
(2) Date: Nov. 30, 2020

(87) PCT Pub. No.: WO2019/229677
PCT Pub. Date: Dec. 5, 2019

(65) Prior Publication Data
US 2021/0196835 A1    Jul. 1, 2021

Related U.S. Application Data

(60) Provisional application No. 62/677,782, filed on May 30, 2018.

(51) Int. Cl.
| | | |
|---|---|---|
| A61P 35/00 | (2006.01) | |
| A61K 31/573 | (2006.01) | |
| A61K 38/19 | (2006.01) | |
| A61K 39/00 | (2006.01) | |
| A61K 47/68 | (2017.01) | |
| C07K 16/28 | (2006.01) | |

(52) U.S. Cl.
CPC .......... *A61K 31/573* (2013.01); *A61K 38/193* (2013.01); *A61K 47/68033* (2023.08); *A61K 47/6867* (2017.08); *A61P 35/00* (2018.01); *C07K 16/2896* (2013.01); *A61K 2039/505* (2013.01)

(58) Field of Classification Search
CPC .............. A61K 47/6867; A61K 38/193; A61K 2039/505; A61P 35/00; C07K 16/2896
See application file for complete search history.

(56) References Cited

U.S. PATENT DOCUMENTS

| | | |
|---|---|---|
| 5,122,368 A | 6/1992 | Greenfield et al. |
| 5,595,756 A | 1/1997 | Bally |
| 7,303,749 B1 | 12/2007 | Chari |
| 7,585,491 B2 | 9/2009 | Govindan |
| 7,601,354 B2 | 10/2009 | Chari |
| 7,989,598 B2 | 8/2011 | Steeves et al. |
| 8,088,387 B2 | 1/2012 | Steeves et al. |
| 8,765,917 B2 | 7/2014 | Deckert et al. |
| 9,346,887 B2 | 5/2016 | Deckert et al. |
| 9,447,189 B2 | 9/2016 | Deckert et al. |
| 10,202,460 B2 | 2/2019 | Deckert et al. |
| 10,556,958 B2 | 2/2020 | Deckert et al. |
| 2003/0114398 A1 | 6/2003 | Chatterjee et al. |
| 2004/0166115 A1 | 8/2004 | Griffiths et al. |
| 2005/0136049 A1 | 6/2005 | Ledbetter et al. |
| 2005/0287538 A1 | 12/2005 | Cheung et al. |
| 2006/0039913 A1 | 2/2006 | Das et al. |
| 2006/0233822 A1 | 10/2006 | Xia et al. |
| 2006/0263349 A1 | 11/2006 | Mccutcheon et al. |
| 2007/0009519 A1 | 1/2007 | Hariharan et al. |
| 2007/0059306 A1 | 3/2007 | Grosmaire et al. |
| 2007/0237779 A1 | 10/2007 | Ledbetter et al. |
| 2007/0270585 A1 | 11/2007 | Chari et al. |
| 2008/0075726 A1 | 3/2008 | Smith et al. |
| 2008/0226626 A1 | 9/2008 | Hariharan et al. |
| 2008/0227198 A1 | 9/2008 | Hariharan et al. |
| 2008/0279850 A1 | 11/2008 | Brady et al. |
| 2009/0041783 A1 | 2/2009 | Takayama et al. |
| 2009/0136516 A1 | 5/2009 | Tedder et al. |
| 2009/0148447 A1 | 6/2009 | Ledbetter et al. |
| 2009/0175867 A1 | 7/2009 | Thompson et al. |
| 2009/0269336 A1 | 10/2009 | Hong et al. |
| 2009/0274692 A1 | 11/2009 | Tan et al. |
| 2009/0274713 A1 | 11/2009 | Chari et al. |
| 2010/0034820 A1 | 2/2010 | Ledbetter et al. |

(Continued)

FOREIGN PATENT DOCUMENTS

| | | |
|---|---|---|
| CN | 1446104 A | 10/2003 |
| CN | 1494433 A | 5/2004 |

(Continued)

OTHER PUBLICATIONS

Ackler, S., et al., "The Bcl-2 Inhibitor ABT-263 Enhances the Response of Multiple Chemotherapeutic Regimens in Hematologic Tumors in Vivo," Cancer Chemotherapy and Pharmacology 66(5):869-880, Springer Verlag, Germany (2010).

(Continued)

*Primary Examiner* — Robert S Landsman
(74) *Attorney, Agent, or Firm* — Sterne Kessler Goldstein & Fox P.L.L.C.

(57) ABSTRACT

Methods of administering immunoconjugates that bind to CD37 are provided. The methods comprise administering an anti-CD37 immunoconjugate, optionally in combination with an anti-CD20 therapy, to a person in need thereof, for example, a cancer patient, at a therapeutically effective dosing regimen that results in minimal adverse effects.

20 Claims, 8 Drawing Sheets

Figure 1:
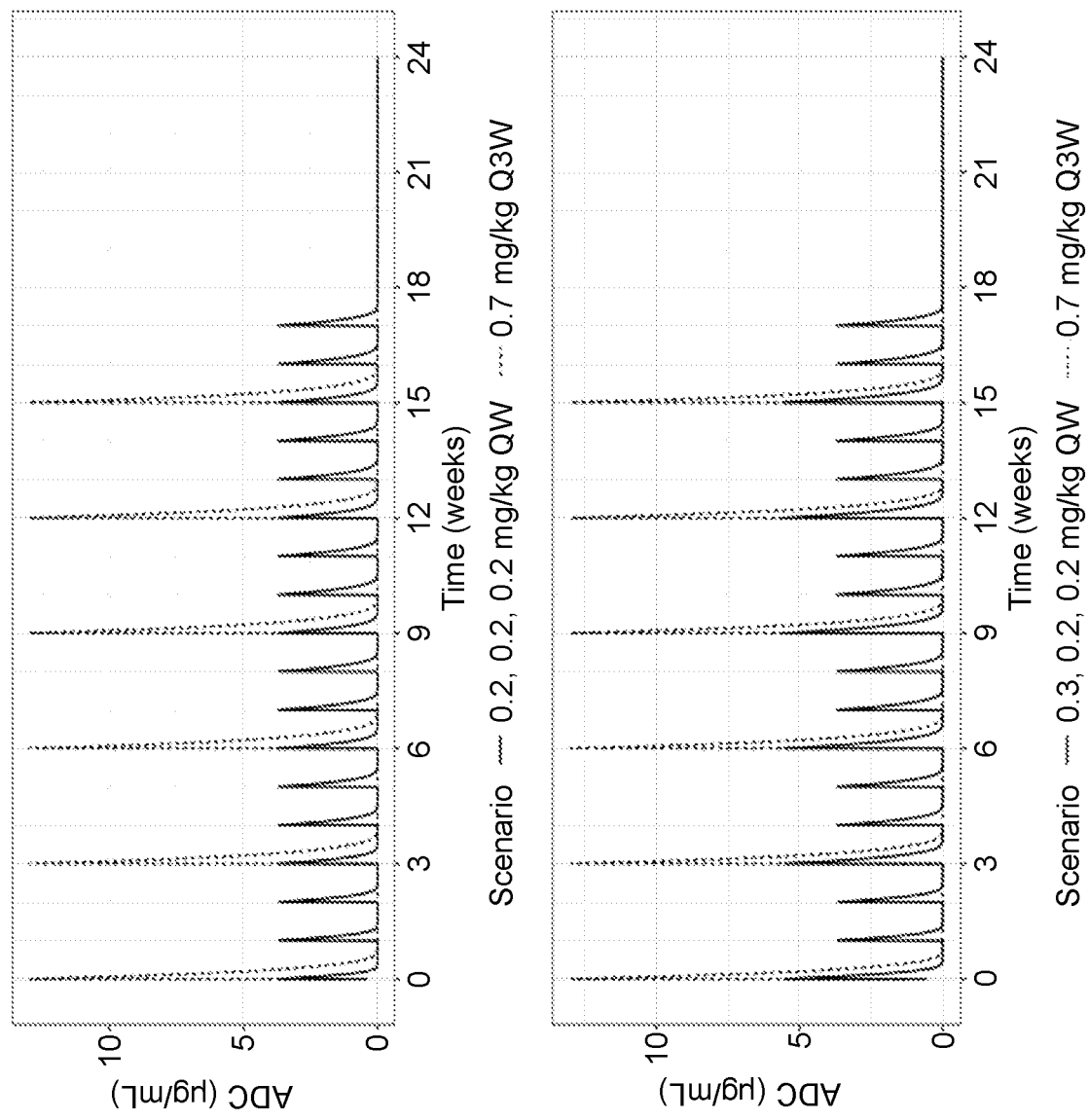

Specification includes a Sequence Listing.

(56) References Cited

U.S. PATENT DOCUMENTS

| | | |
|---|---|---|
| 2010/0135900 A1 | 6/2010 | Cerveny et al. |
| 2010/0189722 A1 | 7/2010 | Heider et al. |
| 2011/0256056 A1 | 10/2011 | Alper et al. |
| 2011/0256153 A1 | 10/2011 | Deckert et al. |
| 2012/0020963 A1 | 1/2012 | Banchereau et al. |
| 2012/0020983 A9 | 1/2012 | Braun et al. |
| 2012/0276119 A1 | 11/2012 | Deckert et al. |
| 2013/0058947 A1 | 3/2013 | Stull et al. |
| 2013/0295104 A1 | 11/2013 | Deckert et al. |
| 2014/0120083 A1 | 5/2014 | Stern et al. |
| 2014/0170063 A1 | 6/2014 | Govindan et al. |
| 2014/0348745 A1 | 11/2014 | Larsen et al. |
| 2015/0093397 A1 | 4/2015 | Carrigan |
| 2015/0343077 A1 | 12/2015 | Deckert et al. |
| 2016/0326258 A1 | 11/2016 | Deckert et al. |
| 2016/0340438 A1 | 11/2016 | Deckert et al. |
| 2017/0000900 A1 | 1/2017 | Romanelli |
| 2018/0244795 A1 | 8/2018 | Deckert et al. |
| 2019/0183788 A1 | 6/2019 | Romanelli et al. |
| 2019/0218303 A1 | 7/2019 | Deckert et al. |
| 2020/0054763 A1 | 2/2020 | Bertoni et al. |
| 2020/0270361 A1 | 8/2020 | Deckert et al. |
| 2020/0330604 A1 | 10/2020 | Li et al. |

FOREIGN PATENT DOCUMENTS

| | | | |
|---|---|---|---|
| CN | 1568198 | A | 1/2005 |
| EP | 0328147 | B1 | 5/1994 |
| JP | 2006513203 | A | 4/2006 |
| JP | 2013524777 | A | 6/2013 |
| JP | 2016536298 | A | 11/2016 |
| WO | WO-0124763 | A2 | 4/2001 |
| WO | WO-0204021 | A1 | 1/2002 |
| WO | WO-02060484 | A1 | 8/2002 |
| WO | WO-02060485 | A2 | 8/2002 |
| WO | WO-02102972 | A2 | 12/2002 |
| WO | WO-03048306 | A2 | 6/2003 |
| WO | WO-03083069 | A2 | 10/2003 |
| WO | WO-2004058298 | A1 | 7/2004 |
| WO | WO-2005017148 | A1 | 2/2005 |
| WO | WO-2005037989 | A2 | 4/2005 |
| WO | WO-2005037992 | A2 | 4/2005 |
| WO | WO-2006074397 | A2 | 7/2006 |
| WO | WO-2006133450 | A2 | 12/2006 |
| WO | WO-2007014278 | A2 | 2/2007 |
| WO | WO-2007077173 | A1 | 7/2007 |
| WO | WO-2007140371 | A2 | 12/2007 |
| WO | WO-2007146968 | A2 | 12/2007 |
| WO | WO-2008052030 | A2 | 5/2008 |
| WO | WO-2008119567 | A2 | 10/2008 |
| WO | WO-2009019312 | A2 | 2/2009 |
| WO | WO-2009065576 | A1 | 5/2009 |
| WO | WO-2009085576 | A2 | 7/2009 |
| WO | WO-2009126858 | A2 | 10/2009 |
| WO | WO-2009126944 | A1 | 10/2009 |
| WO | WO-2009134977 | A1 | 11/2009 |
| WO | WO-2010008726 | A1 | 1/2010 |
| WO | WO-2010009124 | A2 | 1/2010 |
| WO | WO-2010126551 | A1 | 11/2010 |
| WO | WO-2011090754 | A1 | 7/2011 |
| WO | WO-2011090762 | A1 | 7/2011 |
| WO | WO-2011100398 | A1 | 8/2011 |
| WO | WO-2011100403 | A1 | 8/2011 |
| WO | WO-2011112978 | A1 | 9/2011 |
| WO | WO-2012135740 | A2 | 10/2012 |
| WO | WO-2013149171 | A2 | 10/2013 |
| WO | WO-2013171289 | A1 | 11/2013 |
| WO | WO-2014143807 | A2 | 9/2014 |
| WO | WO-2014195460 | A1 | 12/2014 |
| WO | WO-2014197411 | A1 | 12/2014 |
| WO | WO-2015038777 | A1 | 3/2015 |
| WO | WO-2015067586 | A2 | 5/2015 |
| WO | WO-2015116729 | A2 | 8/2015 |
| WO | WO-2015175533 | A2 | 11/2015 |
| WO | WO-2016200676 | A1 | 12/2016 |
| WO | WO-2017040247 | A1 | 3/2017 |
| WO | WO-2018083633 | A1 | 5/2018 |
| WO | WO-2019229677 | A1 | 12/2019 |

OTHER PUBLICATIONS

Algate, P., et al., "TRU-016, An Anti-CD37 Smip (TM) Biologic, In combination with Other therapeutic Drugs in Models of Non-Hodgkin's Lymphoma," Blood 116(21):3931, American Society of Hematology, United States (Nov. 2010), 5 pages.

Alley, S.C., et al., "Antibody-drug Conjugates: Targeted Drug Delivery for Cancer," Current Opinion in Chemical Biology 14(4):529-537, Elsevier, England (2010).

Altschuler, E.P., et al., "Method for Obtaining Recombinant Antibodies and for Improving Affinities Thereof," Uspehi biologicheskoi himii 50: 203-258, Pleiades Publishing Ltd., Russia (Dec. 2010).

Altschuler, E.P., et al., "Generation of Recombinant Antibodies and Means for Increasing Their Affinity," Biochemistry 75(13):1584-1605, Pleiades Publishing, Ltd., United States (Dec. 2010).

Angeletti, R.H., "Design of Useful Peptide Antigens," Journal of Biomolecular Techniques 10(1):2-10, Association of Biomolecular Resource Facilities, United States (1999).

Angelisova, P., et al., "Association of Four Antigens of the Tetraspans Family (CD37, CD53, TAPA-1, and R2/C33) with MHC Class II Glycoproteins," Immunogenetics 39(4):249-256, Springer-Verlag, Germany (1994).

Awan, F., et al., "Phase 1 Study of TRU-016, an Anti-CD37 SMIP Protein in Naive and Relapsed and/or Refractory CLL Patients," ASH Annual Meeting 642: Abstract#1792 poster, p. 1, United States (Nov. 2011). Accessed at: https://ash.confex.com/ash/2011/webprogram/Paper39421.html on Jul. 20, 2015.

Awan, F., et al., "Phase 1 Study of TRU-016, an Anti-CD37 SMIP Protein in Naive and Relapsed and/or Refractory CLL Patients," Poster 1792, 1 p. 2011 American Society of Hematology Annual Meeting, Dec. 10 San Diego, United States.

Awan, F.T., et al., "Phase 1 Study of TRU-016, an Anti-CD37 SMIP™ Protein in Naive and Relapsed and/or Refractory CLL Patients," Blood (ASH Annual Meeting Abstracts) 118(21):Abstract 1792, pp. 1-2, United States (Nov. 2011), Accessed at http://www.bloodjournal.org/content/118/21/1792.full.pdf on Dec. 2, 2015.

Barrena, S., et al., "Aberrant Expression of Tetraspanin Molecules in B-cell Chronic Lymphoproliferative Disorders and its Correlation with Normal B-cell Maturation," Leukemia 19(8):1376-1383, Nature Publishing Group, England (2005).

Beckwith, K.A., et al.," The CD37-Targeted Antibody-Drug Conjugate IMGN529 is Highly Active against Human CLL and in a Novel CD37 Transgenic Murine Leukemia Model," Leukemia 28(7):1501-1510, Nature Publishing Group, England (Jul. 2014).

Beers, S.A., et al., "Type II (Tositumomab) Anti-CD20 Monoclonal Antibody Out Performs Type I (Rituximab-Like) Reagents in B-Cell Depletion Regardless of Complement Activation," Blood 112(10):4170-4177, American Society of Hematology, United States (2008).

Bernstein, I.D., et al., "High Dose Radiolabeled Antibody Therapy of Lymphoma," Cancer Research 50(3 Suppl):1017s-1021s, American Association for Cancer Research, United States (1990).

Bissery, M., et al., "Experimental Antitumor Activity of Taxotere (RP 56976, NSC 628503), a Taxol Analogue," Cancer Research 51(18):4845-4852, American Association for Cancer Research, United States (1991).

Blanc, V., et al., "SAR3419: An Anti-CD19-Maytansinoid Immunoconjugate for the Treatment of B-Cell Malignancies," Clinical Cancer Research 17(20):6448-6458, American Association for Cancer Research, United States (2011).

Boross, P. and Leusen, J.H., "Mechanisms of Action of CD20 Antibodies," American Journal of Cancer Research 2(6):676-690, e-Century Publishing Corporation, United States (2012).

Braslawsky, G.R., et al., "Antitumor Activity of Adriamycin (hydrazone-linked) Immunoconjugates Compared with Free Adriamycin and Specificity of Tumor Cell Killing," Cancer Research 50(20):6608-6614, American Association for Cancer Research, United States (1990).

(56) References Cited

OTHER PUBLICATIONS

Business Wire, "ImmunoGen, Inc. Announces Presentations at the 102nd Annual Meeting of the American Associated for Cancer Research," May 30, 2011, accessed at http://files.shareholder. cornjdownloads/ABEA-5VU3S1/0x0x500536/b6f7f6a6-1853-4476-93cf-2f2f895241d7/1MGN News_2011_3_30_General_Releases. pdf, accessed on Dec. 8, 2014.

Chen, R., et al., "A Phase II Study of Vorinostat and Rituximab for Treatment of Newly Diagnosed and Relapsed/refractory Indolent Non-hodgkin Lymphoma," Haematologica 100(3):357-362, Ferrata Storti Foundation, Italy (Mar. 2015).

Cheson, B.D., et al., "Revised Response Criteria for Malignant Lymphoma," Journal of Clinical Oncology 25(5):579-586, American Society of Clinical Oncology, United States (2007).

Co, M.S., et al., "Chimeric and Humanized Antibodies With Specificity for the CD33 Antigen," Journal of immunology (Baltimore, Md. : 1950), 148(4):1149-1154., American Association of Immunologists, United States (Feb. 1992).

Colman, P.M., "Effects of Amino Acid Sequence Changes on Antibody-antigen Interactions," Research in Immunology 145(1):33-36, Elsevier, France (Jan. 1994).

Cragg, M.S., et al., "Complement-mediated Lysis by Anti-CD20 mAb Correlates with Segregation into Lipid Rafts," Blood 101(3):1045-1052, American Society of Hematology, United States (Feb. 2003).

Dahle, J., et al., "Evaluating Antigen Targeting and Anti-tumor Activity of a New Anti-CD37 Radioimmunoconjugate Against Non-Hodgkin's Lymphoma," Anticancer Research 33(1):85-96, International Institute of Anticancer Research, Greece (2013).

Daniel, C., et al., "Mapping of Linear Antigenic Sites on the S Glycoprotein of a Neurotropic Murine Coronavirus with Synthetic Peptides: a Combination of Nine Prediction Algorithms Fails To Identify Relevant Episodes and Peptide Immunogenicity Is Drastically Influenced by the Nature of the Protein Carrier," Virology 202:540-549, Elsevier Inc., Netherlands (1994).

De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).

Deckert, J., et al., IMGN529, a Novel Antibody-Drug Conjugate (ADC) Targeting CD37 Shows Synergistic Activity with Rituximab in Non-Hodgkin Lymphoma (NHL) Models, poster# 1548. 1 page 57th ASH Annual Meeting and Exposition, Dec. 5, 2015, Orlando, United States.

Deckert, J., et al.,"Preclinical Mechanistic Studies Investigating Neutrophil and Lymphoid Cell Depletion by IMGN529, a CD37-Targeting Antibody-Drug Conjugate (ADC)," poster# 3119, 2 pages, 57th ASH Annual Meeting and Exposition, Dec. 6-9, 2014, San Francisco, United States.

Deckert, J., et al., "A Novel Anti-CD37 Antibody-Drug Conjugate with Multiple Anti-tumor Mechanisms for the Treatment of B-Cell Malignancies," Blood 122(20):3500-3510, American Society of Hematology, United States (2013).

Deckert, J., et al., "IMGN529, a Novel Antibody-Drug Conjugate (ADC) Targeting CD37 Shows Synergistic Activity with Rituximab in Non-Hodgkin Lymphoma (NHL) Models," Blood 126(23):1548, 4 pages American Society of Hematology, United States (Dec. 2015).

Deckert, J., et al., "IMGN529: a Therapeutic Maytansinoid Conjugate of an Anti-CD37 Antibody with Multiple Mechanisms of Action for B-cell Lymphoma and Leukemia," AACR Poster Abstract #2, United States, Apr. 2-6, 2011.

Deckert, J., et al., "IMGN529: an Anti-CD37 Antibody-Maytansinoid Conjugate with Multiple Mechanisms of Actions for B-Cell Malignancies," Keystone Symposia—B Cells: New Insights into Normal versus Dysregulated Function, Apr. 12-16, 2011, Poster #306, United States (Apr. 2011).

Deckert, J., et al., "Potent B-Cell Depletion by IMGN529, a CD37-Targeting Antibody-Maytansinoid Conjugate for the Treatment of B-Cell Malignancies," ASH 2011, Abstract #3726, pp. 1-2, United States (Nov. 2011).

Deckert, J., et al., "Preclinical Mechanistic Studies Investigating Neutrophil and Lymphoid Cell Depletion by IMGN529, a CD37-Targeting Antibody-Drug Conjugate (ADC)," 56th ASH Annual Meeting and Exposition: Abstract# 3119, 1 page, United States (Dec. 2014) Accessed at https://ash.confex.com/ash/2014/webprogram/Paper70777.html on Aug. 26, 2015.

Deckert, J., et al., "Preclinical Mechanistic Studies Investigating Neutrophil and Lymphoid Cell Depletion by IMGN529, a CD37-Targeting Antibody-Drug Conjugate (ADC)," 56th ASH Annual Meeting and Exposition: Poster p. 1, Abstract# 3119, Accessed at http://www.immunogen.com/documents/Publications/IMGN529%20preclinical%20ASH%2012-2014.pdf on Aug. 26, 2015.

Deckert, J., et al., "Preclinical Mechanistic Studies Investigating Neutrophil and Lymphoid Cell Depletion by IMGN529, a CD37-Targeting Antibody-Drug Conjugate (ADC),"poster# 1548. 1 page 57th ASH Annual Meeting and Exposition, Dec. 6-9, 2014, San Francisco , United States.

Dijoseph, J.F., et al., "CD20-specific Antibody-targeted Chemotherapy of Non-Hodgkin's B-cell Lymphoma Using Calicheamicin-conjugated Rituximab," Cancer Immunol Immunother 56(7):1107-1117, Springer-Verlag, Germany (2007).

Ducry, L., et al., "Antibody-Drug Conjugates: Linking Cytotoxic Payloads to Monoclonal Antibodies," Bioconjugate 21:5-13, American Chemical Society, United States (2009).

Epstein, A.L., et al., "Two New Monoclonal Antibodies, Lym-1 and Lym-2, Reactive With Human B-lymphocytes and Derived Tumors, With Immunodiagnostic and Immunotherapeutic Potential," Cancer Research 47(3):830-840, American Association for Cancer Research, United States (Feb. 1987).

Epstein, A.L., et al., "Two New Monoclonal Antibodies (LN-1, LN-2) Reactive in B5 Formalin-fixed, Paraffin-embedded Tissues with Follicular Center and Mantle Zone Human B Lymphocytes and Derived Tumors," Journal of Immunology 133(2):1028-1036, American Association of Immunologists, United States (1984).

Eugenio, G., et al., Identification of anti-lymphoma biomarkers of response to the anti-cd37 antibody drug conjugate (ADC) IMGN529, presented at 58th Annual Meeting and Exposition of the American Society of Hematology 128, 1 page (2016).

Extended European Search Report and Written Opinion for EP Application No. 13 77 0074, The Hague, Netherlands, completed on Oct. 20, 2015, pp. 1-9.

Friedberg, J.W., "Double-Hit Diffuse Large B-cell Lymphoma," Journal of Clinical Oncology 30(28):3439-3443, American Society of Clinical Oncology, United States (2012).

Gershoni, J.M., et al., "Epitope Mapping: the First Step in Developing Epitope-based Vaccines," BioDrugs 21(3):145-156, Springer International, New Zealand (2007).

Goel, M., et al., "Plasticity Within the Antigen-combining Site May Manifest as Molecular Mimicry in the Humoral Immune Response," Journal of Immunology 173(12):7358-7367, American Association of Immunologists, United States (Dec. 2004).

Gopal, A., et al., "Phase 1b Study of otlertuzumab (TRU-016), an Anti-CD37 monospecific ADAPTIRTM therapeutic protein, in Combination with Rituximab and Bendamustine in Relapsed Indolent Lymphoma patients," Investigational New Drugs Presented at ASH annual meeting 2012, 13 pages.

Green, T.M., et al., "Immunohistochemical Double-Hit Score is a Strong Predictor of Outcome in Patients with Diffuse Large B-cell Lymphoma Treated with Rituximab Plus Cyclophosphamide, Doxorubicin, Vincristine, and Prednisone," Journal of Clinical Oncology 30(28):3460-3467, American Society of Clinical Oncology, United States (2012).

Greenfield, R.S., et al., "Evaluation in Vitro of Adriamycin Immunoconjugates Synthesized Using an Acid-sensitive Hydrazone Linker," Cancer Research 50(20):6600-6607, American Association for Cancer Research, United States (1990).

Greenspan, N.S. and Di Cera, E., "Defining Epitopes: It's not as Easy as it Seems," Nature Biotechnology 17(10):936-937, Nature Publishing Group, United States (1999).

(56) References Cited

OTHER PUBLICATIONS

Gross, J., "3333: Evaluation of Otlertuzumab (TRU-016), an Anti-CD37 ADAPTIRTM Therapeutic in Preclinical Combination Studies with Kinase Inhibitors and a Next Generation Anti-CD20 Mab in Vitro and in Animal Models of Non-Hodgkin's Lymphoma," Blood 124(21):3333, 2 pages, American Society of Hematology, United States (2014).

Gussow, D. and Seemann, G., "Humanization of Monoclonal Antibodies," Methods in Enzymology 203:99-121, Elsevier Science, United States (1991).

Harris, C.L., et al., "Tumour Cell Killing Using Chemically Engineered Antibody Constructs Specific for Tumour Cells and the Complement Inhibitor CD59," Clinical & Experimental Immunology 107(2):364-371, Blackwell Publishing, England (1997).

Heider, K.H., et al., "A Novel Fc-engineered Monoclonal Antibody to CD37 with Enhanced ADCC and High Proapoptotic Activity for Treatment of B-cell Malignancies," Blood 118(15):4159-4168, The American Society of Hematology, United States (2011).

Hicks, S.W., et al., "The Antitumor Activity of Imgn529, a Cd37-targeting Antibody-drug Conjugate, Is Potentiated by Rituximab in Non-Hodgkin Lymphoma Models," Neoplasia 19(9):661-671, Neoplasia Press, United States (Sep. 2017).

Hu, S., et al., "MYC/BCL2 Protein Coexpression Contributes to the Inferior Survival of Activated B-Cell Subtype of Diffuse Large B-Cell Lymphoma and Demonstrates High-Risk Gene Expression Signatures: a Report from The International DLBCL Rituximab-CHOP Consortium Program," Blood 121(20):4021-4031, American Society of Hematology, United States (2013).

International Preliminary Report on Patentability for International Application No. PCT/US2012/031648, The International Bureau of WIPO, Switzerland, mailed Oct. 2, 2013, pp. 1-9.

International Preliminary report on patentability for International Application No. PCT/US2016/035558, International search authority, Switzerland, mailed on Dec. 12, 2017, 8 pages.

International Preliminary Report on Patentability for International Application No. PCT/US2016/048887, International Searching Authority, United States, mailed Nov. 29, 2016, 5 pages.

International Search Report and Written Opinion for International Application No. PCT/US11/28172, International Searching Authority, United States, mailed Jul. 13, 2011, pp. 1-9.

International Search Report and Written Opinion for International Application No. PCT/US12/31648, Commissioner for Patents, United States, mailed Sep. 20, 2012, 17 pages.

International Search Report and Written Opinion for International Application No. PCT/US15/30371, Commissioner for Patents, United States, mailed on Nov. 2, 2015, pp. 1-10.

International Search Report and Written Opinion for International Application No. PCT/US2013/034646, Commissioner for Patents, United States, mailed on Sep. 16, 2013.

International Search Report and Written Opinion for International Application No. PCT/US2016/035558, Commissioner for Patents, United States, mailed on Sep. 7, 2016, 11 pages.

International Search Report and Written Opinion for International Application No. PCT/US2016/048887, Commissioner for Patents, United States, mailed on Nov. 29, 2016, 8 pages.

International Search Report with Written Opinion for International Application No. PCT/IB2017/056841, International Searching Authority, Netherlands, mailed Feb. 2, 2018, 10 pages.

Kaminski, M.S., et al., "Imaging, Dosimetry, and Radioimmunotherapy with Iodine 131-labeled Anti-CD37 Antibody in B-cell Lymphoma," Journal of Clinical Oncology 10(11):1696-1711, American Society of Clinical Oncology, United States (1992).

Khan, T and Salunke, D.M, "Adjustable Locks and Flexible Keys: Plasticity of Epitope-paratope Interactions in Germline Antibodies," Journal of Immunology 192(11):5398-5405, American Association of Immunologists, United States (Jun. 2014).

Knobeloch, K.P., et al., "Targeted Inactivation of the Tetraspanin CD37 Impairs T-cell-dependent B-cell Response Under Suboptimal Costimulatory Conditions," Molecular and Cellular Biology 20(15):5363-5369, American Society for Microbiology, United States (2000).

Konig, A., et al., "Basic Fibroblast Growth Factor (bFGF) Upregulates the Expression of bcl-2 in B Cell Chronic Lymphocytic Leukemia Cell Lines Resulting in Delaying Apoptosis," Leukemia 11(2):258-265, Nature Publishing Group, England (1997).

Kovtun, Y., et al., "Antibody-Maytansinoid Conjugates Designed to Bypass Multidrug Resistance," Cancer Research 70(6):2528-2537, American Association for Cancer Research, United States (Mar. 2010).

Lai, K.C., et al., "Evaluation of Targets for Maytansinoid ADC Therapy Using a Novel Radiochemical Assay," Pharmaceutical Research 32(11):3593-3603, Kluwer Academic, United States (2015).

Lai, K.C., et al., "The CD37-targeting ADC IMGN529 Combines the Potent Anti-cancer Activity of K7153A Antibody with Efficient Maytansinoid Delivery," American Association for Cancer Research Hosted by the European Organization for Research and Treatment of Cancer and the National Cancer Institute, Abstract #B209 Poster, 1 page, United States (Nov. 2011). Accessed at: http://mct.aacrjournals.org/content/10/11_Supplement/B209.short on Jul. 20, 2015.

International Search Report and Written Opinion mailed Aug. 21, 2019, in International Application No. PCT/IB2019/054457, EPO, Netherlands, 11 pages.

Lai, K.C., et al., "The CD37-targeting ADC IMGN529 Combines the Potent Anti-cancer Activity of K7153A Antibody with Efficient Maytansinoid Delivery," Oasis, The Online Abstract Submission System, Abstract 11-A-226-AACR:pp. 1-2, Molecular Targets and Cancer Therapeutics, Nov. 12-16, 2011, San Francisco, United States (Nov. 2011). Accessed at http://www.abstractsonline.com/plan/viewabstract.aspx?mid=2889&skey=946d141d-1376-4bec-8e3f-a54580b89072&ckey=5af84375-1153-46e6-974c-e95ea6225aef&mkey=%7Ba57ff86d-d414-4079-bcbd-157746574f37%7D on Jul. 16, 2015.

Lambert, J.M., "Antibody-Maytansinoid Conjugates: a New Strategy for the Treatment of Cancer," Drugs of the Future 35(6):471-480, Prous Science, S.A.U., Spain (Jun. 2010).

Lapalombella, R., et al., "Tetraspanin CD37 Directly Mediates Transduction of Survival and Apoptotic Signals," Cancer Cell 21(5):694-708, Elsevier Inc., United States (2012).

Lim, S.H., et al., "Anti-CD20 Monoclonal Antibodies: Historical and Future Perspectives," Haematologica 95(1):135-143, Ferrata Storti Foundation, Italy (Jan. 2010).

Link, M.P., et al., "A Unique Antigen on Mature B Cells Defined by a Monoclonal Antibody," The Journal of Immunology 137(9):3013-3018, The American Association of Immunologists, United States (1986).

Lippincott-Schwartz, J., "Antibodies as Cell Biological Tools," Current Protocols in Cell Biology, 16.0.1-16.0.2, 2002.

Maccallum, R.M., et al., "Antibody-antigen Interactions: Contact Analysis and Binding Site Topography," Journal of Molecular Biology 262(5):732-745, Academic Press, England (Oct. 1996).

Maecker, H.T., et al., "The Tetraspanin Superfamily: Molecular Facilitators," FASEB Journal 11(6):428-442, The Federation, United States (1997).

Mariuzza, R.A., et al., "The Structural Basis of Antigen-antibody Recognition," Annual Review of Biophysics and Biomolecular Structure 16:139-159, Annual Reviews, United States (1987).

Marken, J.S., et al., "Membrane Topology of the L6 Antigen and Identification of the Protein Epitope Recognized by the L6 Monoclonal Antibody," The Journal of Biological Chemistry 269(10):7397-7401, American Society for Biochemistry and Molecular Biology, United States (1994).

Meyer-Wentrup, F., et al., "Dectin-1 Interaction with Tetraspanin CD37 Inhibits IL-6 Production," The Journal of Immunology 178(1):154-162, The American Association of Immunologists, Inc., United States (2007).

Moore, K., et al., "Use of the Monoclonal Antibody WR17, Identifying the CD37 gp40-45 Kd Antigen Complex, in the Diagnosis of B-lymphoid Malignancy," Journal of Pathology 152(1):13-21, John Wiley & Sons, Ltd., England (1987).

(56) References Cited

OTHER PUBLICATIONS

Morris, G.E., "Epitope Mapping of Protein Antigens by Competition ELISA," The Protein Protocols Handbook 1:595-600, Humana Press, United States (1996).
NCT01534715, "IMGN529 in Treating Patients with Relapsed or Refractory Non-Hodgkin's Lymphoma," retrieved from https://clinical.gov/archive/NCT01534715/2012_02_16, retrieved on Sep. 6, 2016, 2 pages.
Oki, Y., et al., "Pegylated Liposomal Doxorubicin Replacing Conventional Doxorubicin in Standard R-chop Chemotherapy for Elderly Patients With Diffuse Large B-cell Lymphoma: an Open Label, Single Arm, Phase II Trial," Clinical Lymphoma, Myeloma & Leukemia 152-158, Elsevier, United States (Mar. 2015).
Pagel, J.M, et al., "Phase 1 Study of TRU-016, an Anti-CD37 SMIP™ Protein in Relapsed and/or Refractory NHL Patients," Blood (ASH Annual Meeting Abstracts) 2011 118(21):Abstract 1636, The American Society of Hematology, United States (2011).
Park, P.U., et al., "Antibody and Linker Selection for the Anti-CD37 Antibody-maytansinoid Conjugate IMGN529 for the Treatment of B-cell Malignancies," Experimental and Molecular Therapeutics Session, AACR Annual Meeting 2011, Experimental and Molecular Therapeutics session, Abstract #2830:1-24, United States (Apr. 2011). Accessed at http://cancerres.aacrjournals.org/content/71/8_Supplement/2830.abstract on Jul. 20, 2015.
Paul, W.E., "Immunogenicity and Antigen Structure," in Fundamental Immunology, Third Edition, pp. 242, Raven Press, United States (1993).
Pers, J.O., et al., "Anti-CD20 Antibody-Mediated Apoptosis of B Cells Is a Lipid Raft-Dependent Process," Annals of the Rheumatic Diseases 70(Suppl 2):A73, BMJ Publishing Group Ltd (Feb. 2011).
Pinkas, J., "Antibody Maytansinoid Conjugates for the Treatment of Cancer," Protein Therapeutics Forum 2012:1-23, Jan. 30, 2012, United States (Jan. 2012).
Polson, A.G., et al., "Antibody-drug Conjugates For the Treatment of Non-Hodgkin's Lymphoma: Target and Linker-drug Selection," Cancer Research 69(6):2358-2364, American Association for Cancer Research, United States (2009).
Poosarla, V.G., et al., "Computational De Novo Design of Antibodies Binding to a Peptide With High Affinity," Biotechnology and Bioengineering 114(6):1331-1342, Wiley, United States (Jun. 2017).
Preissuance Submission by Third Party under 37 C.F.R. § 1.290 in U.S. Appl. No. 13/045,693 (inventors Deckert et al., filed Mar. 11, 2011) dated May 30, 2013, 14 pages.
Preissuance Submission by Third Party under 37 C.F.R. § 1.290 in U.S. Appl. No. 13/436,528 (inventors Deckert et al., filed Mar. 30, 2012), dated Aug. 26, 2013, 15 pages.
Preissuance Submission by Third Party under 37 C.F.R. § 1.290 in U.S. Appl. No. 13/796,768 (inventors Deckert et al., filed Mar. 12, 2013), dated Apr. 1, 2014, 18 pages.
Press, O.W., et al., "Endocytosis and Degradation of Monoclonal Antibodies Targeting Human B-cell Malignancies," Cancer Research 49(17):4906-4912, American Association for Cancer Research, United States (1989).
Press, O.W., et al., "Radiolabeled-antibody Therapy of B-cell Lymphoma with Autologous Bone Marrow Support," The New England Journal of Medicine 329(17):1219-1224, Massachusetts Medical Society, United States (1993).
Press, O.W., et al., "Retention of B-cell-specific Monoclonal Antibodies by Human Lymphoma Cells," Blood 83(5):1390-1397, The American Society of Hematology, United States (1994).
Press, O.W., et al., "Treatment of Refractory Non-Hodgkin's Lymphoma with Radiolabeled MB-1 (anti-CD37) Antibody," Journal of Clinical Oncology 7(8):1027-1038, American Society of Clinical Oncology, United States (1989).
Robak, T. and Robak, E., "New Anti-CD20 Monoclonal Antibodies for the Treatment of B-cell Lymphoid Malignancies," BioDrugs 25(1):13-25, Springer International, New Zealand (Feb. 2011).
Robak, T., et al., "TRU-016, a Humanized Anti-CD37 IgG Fusion Protein for the Potential Treatment of B-cell Malignancies," Current Opinion in Investigational Drugs 10(12):1383-1390, Thomson Reuters Ltd., England (2009).
Roguska, M.A., et al., "A Comparison of Two Murine Monoclonal Antibodies Humanized by CDR-grafting and Variable Domain Resurfacing," Protein Engineering 9(10):895-904, Oxford University Press, England (1996).
Roguska, M.A., et al., "Humanization of Murine Monoclonal Antibodies through Variable Domain Resurfacing," Proceedings of the National Academy of Sciences USA 91(3):969-973, National Academy of Sciences, United States (Feb. 1994).
Romanelli, A., et al., Novel CD37-Targeting Antibody-Drug Conjugate (ADC), IMGN529, Has Synergistic Activity in Combination with Rituximab in Non-Hodgkin Lymphoma (NHL) Models, presented at 13th International Conference on Malignant Lymphoma, Jun. 17-20, 2015, 1 page.
Rops, A.L., et al., "The Tetraspanin CD37 Protects Against Glomerular IgA Deposition and Renal Pathology," American Journal of Pathology 176(5):2188-2197, American Society for Investigative Pathology, United States (May 2010).
Rudikoff, S., et al., "Single Amino Acid Substitution Altering Antigen-binding Specificity," Proceedings of the National Academy of Sciences of the United States of America 79(6):1979-1983, National Academy of Sciences, Washington (Mar. 1982).
Rudolph, C., et al., "Molecular Cytogenetic Characterization of the Mantle Cell Lymphoma Cell Line GRANTA-519," Cancer Genetics and Cytogenetics 153(2):144-150, Elsevier, United States (2004).
Schwartz-Albiez, R., et al., "The B Cell-associated CD37 Antigen (gp40-52). Structure and Subcellular Expression of an Extensively Glycosylated Glycoprotein," The Journal of Immunology 140(3):905-914, The American Association of Immunolmists, United States (1988).
Sheng, K-C., et al., "Tetraspanins CD37 and CD151 Differentially Regulate Ag Presentation and T-cell co-stimulation by DC," European Journal of Immunology 39(1):50-55, Wiley-VCH Verlag Gmbh & Co. KGaA, Germany (2009).
Smith, S.M., et al., "The Impact of MYC Expression in Lymphoma Biology: Beyond Burkitt Lymphoma,"Blood Cells, Molecules and Diseases 45(4):317-323, Academic Press, United States (Dec. 2010).
Smith, T.J., et al., "2006 Update of Recommendations for the Use of White Blood Cell Growth Factors: an Evidence-based Clinical Practice Guideline," Journal of Clinical Oncology 24(19):3187-3205, American Society of Clinical Oncology, United States (2006).
Smolewski, P., et al., "Pro-apoptotic Effect of an Anti-cd37 Scfv-fc Fusion Protein, in Combination With the Anti-cd20 Antibody, Ofatumumab, on Tumour Cells From B-cell Malignancies," European Journal of Cancer 50(15):2677-2684, Elsevier, Netherlands (Oct. 2014).
Stathis, A. et al., " Preliminary Findings from a Phase I, Multicenter, Open-label Study of the anti-CD37 Antibody-Drug Conjugate (ADC), IMGN529, in Adult Patients with Relapsed or Refractory Non-Hodgkin Lymphoma (NHL)," 2014 ASCO Annual Meeting, Poster, Abstract No. 8526, United States (May 2014), 1 page Accessed at http://www.immunogen.com/documents/Publications/IMGN529%20first%20clin%20ASCO%202014.pdf on Aug. 26, 2015.
Stathis, A. et al., "A Phase I Study Of IMGN529, an Antibody-Drug Conjugate (ADC) Targeting CD37, In Adult Patients With Relapsed or Refractory Non-Hodgkin Lymphoma (NHL)," 56th ASH Annual Meeting and Exposition: Abstract#1760, United States (Dec. 2014), 1 page Accessed at https://ash.confex.com/ash/2014/webprogram/Paper70219.html, on Aug. 26, 2015.
Stathis, A. et al., "A Phase I Study of IMGN529, an Antibody-Drug Conjugate (ADC) Targeting CD37, in Adult Patients With Relapsed or Refractory Non-Hodgkin Lymphoma (NHL)," Abstract#1760, ASH Annual Meeting, San Francisco, California, United States (Dec. 2014), 2 pages, accessed at http://www.immunogen.com/documents/Publications/IMGN529_Phl_ASH12-2014.pdf, accessed on Aug. 26, 2015.
Stathis, A., et al., "Safety, Tolerability, and Preliminary Activity of IMGN529, a CD37-Targeted Antibody-Drug Conjugate, in Patients with Relapsed or Refractory B-Cell Non-Hodgkin Lymphoma: a

(56) References Cited

OTHER PUBLICATIONS

Dose-Escalation, Phase I Study," Invest New Drugs, 36(5):869-876, Springer, United States (Oct. 2018).
Supplementary European Search Report for Application No. EP11754195, mailed on Sep. 10, 2013, 7 pages.
Tedder, T.F., et al., "Structure of the Gene Encoding the Human B Lymphocyte Differentiation Antigen CD20 (B1)," The Journal of Immunology 142(7):2560-2568, The American Association of Immunologists, United States (1989).
Tedoldi, S., et al., "Selective Loss of B-Cell Phenotype in Lymphocyte Predominant Hodgkin Lymphoma," Pathology 213(4):429-440, John Wiley and Sons, England, (Dec. 2007).
Teicher, B.A. and Chari, R.V.J., "Antibody Conjugate Therapeutics: Challenges and Potential," Clinical Cancer Research 17(20):6389-6397, American Association for Cancer Research, United States (Oct. 2011).
Tomayko. M.M. and Reynolds, C.P., "Determination of Subcutaneous Tumor Size in Athymic (Nude) Mice," Cancer Chemotherapy and Pharmacology 24(3):148-154, Springer Verlag, Germany (1989).
Tutt, A., et al., "Trispecific F(ab')3 Derivatives that use Cooperative Signaling via the TCR/CD3 Complex and CD2 to Activate and Redirect Resting Cytotoxic T Cells," The Journal of Immunology 147:60-69, The American Association of Immunologists, United States (Jul. 1991).
Van Spriel, A.B., et al., "A Regulatory Role for CD37 in T Cell Proliferation," The Journal of Immunology 172 (5):2953-2961, The American Association of Immunologists, United States (2004).
Van Spriel, A.B., et al., "The Tetraspanin Protein CD37 Regulates IgA Responses and Anti-Fungal Immunity," PLoS Pathogens 5(3) e1000338:1-11, Public Library of Science, United States (2009).
Wang, L., et al., "Structural Characterization of the Maytansinoid-Monoclonal Antibody Immunoconjugate, huN901-DM1, by mass spectrometry," Protein Science, 14(9):2436-2446, Cold Spring Harbor Laboratory Press, United States (Sep. 2005).
Wang, Z., et al., "Universal Pcr Amplification of Mouse Immunoglobulin Gene Variable Regions: the Design of Degenerate Primers and an Assessment of the Effect of DNA Polymerase 3' to 5' Exonuclease Activity," Journal of Immunological Methods 233(1-2):167-177, Elsevier, Netherlands (Jan. 2000).
Written Opinion for Singapore Patent Application No. 10201501803Y, dated Sep. 4, 2018, Intellectual Property Office of Singapore, Singapore, 6 pages.
Yu, B., et al., "Targeted Drug Delivery and Cross-Linking Induced Apoptosis with Anti-CD37 based Dual-Ligand Immunoliposomes in B Chronic Lymphocytic Leukemia Cells," Biomaterials 34(26):6185-6193, Elsevier Science, Netherlands (2013).
Zenz, T., et al., "Exceptional In Vitro Activity of CD37 Antibodies in CLL," Blood 116(21): 1021-1022, 2010 ASH Annual Meeting Abstracts (Abstract 2460), American Society of Hematology, United States (2010), accessed at https://ashconfex.com/ash/2010/webprogram/Paper29401.html, accessed on Apr. 4, 2016.
Zhao, X., et al., "CD37 is a Potential Therapeutic Target for B-Cell Non-Hodgkin Lymphoma," Blood, 116(21), p. 1, American Society of Hematology, United States (Nov. 2011); 52nd Annual Meeting of the American Society of Hematology (Ash); United States; Dec. 4-7, 2010 Accessed at https://ash.confex.com/ash/2010/webprogram/Paper28315.html, on Nov. 13, 2015.
Zhao, X., et al., "CD37 is a Potential Therapeutic Target for B-Cell Non-Hodgkin Lymphoma," Blood: 2010 ASH Annual Meeting Abstracts 116(21):1277-1278, Abstract No. 3098, American Society of Hematology, United States (Nov. 19, 2010).
Zhao, X., "Targeting CD37 and folate receptor for cancer therapy: strategies based on engineered proteins and liposomes," Europe PubMed Central, accessed at http://europepmc.org/theses/ETH/6183, accessed on Dec. 9, 2014 (2007) [THESIS 6183], pp. 1-296.
Zhao, X., "Targeting CD37 and folate receptor for cancer therapy: strategies based on engineered proteins and liposomes," Ohio Link Electronic Theses & Dissertations Center, document number osu1174678307, pp. 1-314, The Ohio State University, United States (2007). Accessed at https://etd.ohiolink.edu/ap/10?:: NO 10:P10 ACCESSION_NUM:osu1174678307 on Oct. 2, 2015.
Zhao, X.B., et al., "Novel Anti-CD37 Small Modular Immunopharmaceutical (SMP) Induces B-Cell-Specific, Caspase-Independent Apoptosis in Human CLIJ Cells," Blood 104, Abstract 2515, p. 1, ASII Annual Meeting, American Society of Hematology, United States (2004). Accessed at http://abstracts.hematologylibrary.org/cgi/content/short/104/11/2515 on Jul. 16, 2015.
Zhao, X.B et al., "Targeting CD37-positive Lymphoid Malignancies with a Novel Engineered Small Modular Immunopharmaceutical," Blood 110(7):2569-2577, The American Society of Hematology, United States (2007).
Deckert, J., et al., "IMGN529, a Novel Antibody-Drug Conjugate (ADC) Targeting CD37 Shows Synergistic Activity with Rituximab in Non-Hodgkin Lymphoma (NHL) Models," Blood 126(23):1548, poster, 1 page, American Society of Hematology, United States (Dec. 2015).
Heppner, G.H., et al., "Tumor heterogeneity: biological implications and therapeutic consequences," Cancer Metastasis Rev. 2(1):5-23, Martinus Nihoff Publishers, Netherlands (1983).
Jain, R.K., "Barriers to Drug Delivery in Solid Tumors," Scientific American 271(1):58-65, Scientific American Inc, United States (1994).

METHOD FOR TREATING CANCER IN A HUMAN PATIENT BY ADMINISTERING AN ANTI-CD37 IMMUNOCONJUGATE USING VARIOUS DOSING REGIMENS

CROSS REFERENCE TO RELATED APPLICATIONS

This application is a national phase entry of International Application No. PCT/IB2019/054457, filed May 29, 2019, which claims the priority benefit of U.S. Provisional Application No. 62/677,782, filed May 30, 2018, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: 4018_0090001_Seqlisting_ST25.txt; Size: 15,146 bytes; and Date of Creation: Nov. 30, 2020) is herein incorporated by reference in its entirety.

FIELD OF THE INVENTION

The field of the invention generally relates to methods of administering anti-CD37 immunoconjugates (e.g., Debio 1562), e.g., in combination with an anti-CD20 therapy (e.g., rituximab), for the treatment of diseases, such as cancer.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. Non-Hodgkin Lymphoma (NHL) is one of the most common cancers in the United States, where it accounts for about 4% of all cancers. The anti-CD20 antibody rituximab has had a significant effect on patient outcomes, but patients may show primary and secondary resistance.

Leukocyte antigen CD37 ("CD37"), also known as GP52-40, tetraspanin-26, or TSPAN26, is expressed on B cells during the pre-B to peripheral mature B-cell stages, but is absent on terminal differentiation to plasma cells. (Link et al., 1987, J Pathol. 152:12-21). The CD37 antigen is only weakly expressed on T-cells, myeloid cells and granulocytes (Schwartz-Albiez et al. 1988, J. Immunol., 140(3)905-914). However, CD37 is also expressed on malignant B-cells such as those found in non-Hodgkin's lymphoma (NHL) and chronic lymphoid leukemia (CLL) (Moore et al. 1986, J Immunol. 137(9):3013-8). This expression profile suggests that CD37 represents a promising therapeutic target for B-cell malignancies, and currently, there is a clear unmet medical need for more effective therapeutics for B-cell malignancies.

BRIEF SUMMARY OF THE INVENTION

Provided herein are methods for treating cancer in human patients using an anti-CD37 immunoconjugate (e.g., Debio 1562).

In certain instances, a method for treating a cancer in a human patient comprises administering to the patient a pharmaceutical composition comprising an anti-CD37 immunoconjugate once a week in a three-week cycle, wherein: a) 0.2 mg/kg of the immunoconjugate are administered in the first week, 0.2 mg/kg are administered in the second week, and 0.2 mg/kg are administered in the third week; b) 0.3 mg/kg of the immunoconjugate are administered in the first week, 0.3 mg/kg are administered in the second week, and 0.3 mg/kg are administered in the third week; c) 0.3 mg/kg of the immunoconjugate are administered in the first week, 0.3 mg/kg are administered in the second week, and 0.2 mg/kg are administered in the third week; d) 0.3 mg/kg of the immunoconjugate are administered in the first week, 0.2 mg/kg are administered in the second week, and 0.2 mg/kg are administered in the third week; e) 0.4 mg/kg of the immunoconjugate are administered in the first week, 0.3 mg/kg are administered in the second week, and 0.3 mg/kg are administered in the third week; f) 0.4 mg/kg of the immunoconjugate are administered in the first week, 0.3 mg/kg are administered in the second week, and 0.2 mg/kg are administered in the third week; g) 0.4 mg/kg of the immunoconjugate are administered in the first week, 0.2 mg/kg are administered in the second week, and 0.2 mg/kg are administered in the third week; h) 0.5 mg/kg of the immunoconjugate are administered in the first week, 0.3 mg/kg is administered in the second week, and 0.2 mg/kg are administered in the third week; i) 0.5 mg/kg of the immunoconjugate are administered in the first week, 0.2 mg/kg are administered in the second week, and 0.2 mg/kg are administered in the third week; or j) 0.6 mg/kg of the immunoconjugate are administered in the first week, 0.2 mg/kg are administered in the second week, and 0.2 mg/kg are administered in the third week; wherein the immunoconjugate comprises (i) an antibody or antigen-binding fragment thereof comprising a VH-CDR1 comprising the amino acid sequence of SEQ ID NO:2, a VH-CDR2 comprising the amino acid sequence of SEQ ID NO:3, a VH-CDR3 comprising the amino acid sequence of SEQ ID NO:4, a VL-CDR1 comprising the amino acid sequence of SEQ ID NO:5, a VL-CDR2 comprising the amino acid sequence of SEQ ID NO:6, and a VL-CDR3 comprising the amino acid sequence of SEQ ID NO:7 and (ii) a maytansinoid.

In certain instances, the antibody or antigen-binding fragment comprises a variable heavy chain comprising the amino acid sequence of SEQ ID NO:8. In certain instances, the antibody or antigen-binding fragment thereof comprises a variable light chain comprising the amino acid sequence of SEQ ID NO:10. In certain instances, the antibody or antigen-binding fragment comprises a full length heavy chain comprising the amino acid sequence of SEQ ID NO:11. In certain instances, the antibody or antigen-binding fragment comprises a full length light chain comprising the amino acid sequence of SEQ ID NO:12. In certain instances, the antibody comprises a light chain comprising the same amino acid sequence as the light chain encoded by the phuCD37-3LC plasmid deposited as ATCC deposit PTA-10722 and a heavy chain comprising the same amino acid sequence as the heavy chain encoded by the phuCD37-3HCv1.0 deposited as ATCC deposit PTA-10723.

In certain instances, the maytansinoid is DM1. In certain instances, the maytansinoid is linked to the antibody or antigen-binding fragment by an SMCC linker.

In certain instances, the antibody comprises a full length heavy chain comprising the amino acid sequence of SEQ ID NO:11 and a full length light chain comprising the amino acid sequence of SEQ ID NO: 12, the maytansinoid is DM1, and the DM1 is linked to the antibody by an SMCC linker.

In certain instances, the immunoconjugate comprises 1-10 maytansinoids per antibody.

In certain instances, the pharmaceutical composition comprises at least two of the immunoconjugates, and the immunoconjugates comprise an average of 3 to 4 maytansinoids per antibody. In certain instances, the pharmaceutical composition comprises at least two of the immunoconjugates, and the immunoconjugates comprise an average of 3.5 maytansinoids per antibody.

In certain instances, the immunoconjugate is administered for six three-week cycles.

In certain instances, the immunoconjugate is administered intravenously.

In certain instances, the immunoconjugate is administered in combination with an anti-CD20 therapy. In certain instances, the anti-CD20 therapy and the immunoconjugate are administered in separate pharmaceutical compositions.

In certain instances, the anti-CD20 therapy is rituximab. In certain instances, 375 mg/m$^2$ of the rituximab is administered. In certain instances, the rituximab is administered once every three weeks. In certain instances, the rituximab is administered on day one of the three-week cycle. In certain instances, the immunoconjugate and the rituximab are administered on the same day. In certain instances, the rituximab is administered after the immunoconjugate is administered. In certain instances, the rituximab is administered for six three-week cycles. In certain instances, the rituximab is administered once every four weeks (one month), once every two months, or once every three months.

In certain instances, the pharmaceutical composition comprises at least two immunoconjugates and the immunoconjugates comprise an average of 3 to 4 maytansinoids per antibody, wherein the antibody comprises a full length heavy chain comprising the amino acid sequence of SEQ ID NO:11 and a full length light chain comprising the amino acid sequence of SEQ ID NO: 12, wherein the maytansinoid is DM1, and wherein the DM1 is linked to the antibody by an SMCC linker, wherein the immunoconjugate is administered in combination with 375 mg/m$^2$ of rituximab administered once every three weeks on day one of the three-week cycle after administration of the immunoconjugate.

In certain instances, the methods further comprise administering a corticosteroid to the patient. In certain instances, the corticosteroid is administered prior to the administration of the immunoconjugate. In certain instances, the corticosteroid is administered from about 30 to about 60 minutes prior to administration of the immunoconjugate. In certain instances, the immunoconjugate is administered intravenously, and the corticosteroid is administered peri-infusionally. In certain instances, the corticosteroid is administered after the administration of the immunoconjugate. In certain instances, the corticosteroid is administered from about one day to about four days after administration of the immunoconjugate. In certain instances, the corticosteroid is administered on days 2 and 3 following the administration of the immunoconjugate.

In certain instances, the corticosteroid is selected from the group consisting of prednisone, prednisolone, methylprednisolone, beclamethasone, betamethasone, dexamethasone, fludrocortisone, hydrocortisone, and triamcinolone. In certain instances, the corticosteroid is dexamethasone.

In certain instances, the methods further comprise administering a growth factor to the patient. In certain instances, the growth factor is selected from the group consisting of granulocyte colony-stimulating factor (G-CSF), granulocyte-macrophage colony-stimulating factor (GM-CSF), macrophage colony-stimulating factor (M-CSF), filgrastim, and pegfilgrastim. In certain instances, the growth factor is G-CSF.

In certain instances, the cancer is a B cell malignancy. In certain instances, the cancer is leukemia or lymphoma. In certain instances, the cancer is a Non-Hodgkin's lymphoma (NHL). In certain instances, the NHL is relapsed NHL. In certain instances, the NHL is refractory NHL. In certain instances, the cancer is diffuse large B-cell lymphoma (DLBCL). In certain instances, the DLBCL is relapsed DLBCL. In certain instances, the DLBCL is refractory DLBCL. In certain instances, the cancer is selected from the group consisting of relapsed and/or refractory DLBCL, Follicular Lymphoma (FL), Marginal Zone Lymphoma/Mucosa-associated lymphoid tissue (MZL/MALT), or Mantle Cell Lymphoma (MCL). In certain instances, the cancer is selected from the group consisting of precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma, plasmacytoma, plasma cell myeloma, post-transplant lymphoproliferative disorder, Waldenstrom's macroglobulinemia, and anaplastic large-cell lymphoma (ALCL).

In certain instances, the cancer expresses CD37.

In certain instances, the weekly administration of the anti-CD37 immunoconjugate maintains exposure over three weeks. In certain instances, the weekly administration of the anti-CD37 immunoconjugate limits neutropenia and/or other adverse events. In certain instances, the weekly administration of the anti-C37 immunoconjugate prolongs the synergistic effect with rituximab as compared to administration of the anti-CD37 immunoconjugate every three weeks.

In certain instances, the anti-CD37 immunoconjugate is administered weekly for at least one, at least two, at least three, at least four, at least five, at least six, at least seven, at least eight, at least nine, at least ten, at least eleven or at least twelve three-week cycles. In certain instances, the anti-CD37 immunoconjugate is administered at a dose of 0.7 mg/kg once every three weeks after the at least one, at least two, at least three, at least four, at least five, at least six, at least seven, at least eight, at least nine, at least ten, at least eleven or at least twelve three-week cycles of weekly administration. In certain instances, the anti-CD37 immunoconjugate is administered at a dose of 0.7 mg/kg once every three weeks after a complete response, a partial response, or stable disease is observed following weekly administration.

BRIEF DESCRIPTION OF THE DRAWINGS/FIGURES

FIG. 1 shows simulations of Debio 1562 ("ADC") blood concentration in patients as a result of administration of three weekly doses of 0.2 mg/kg for six cycles as compared to administration of 0.7 mg/kg once every three weeks for six cycles (top panel) or administration of three weekly doses of 0.3, 0.2, and 0.2 mg/kg, respectively, for six cycles as compared to administration of 0.7 mg/kg once every three weeks for six cycles (bottom panel).

Figure 2:
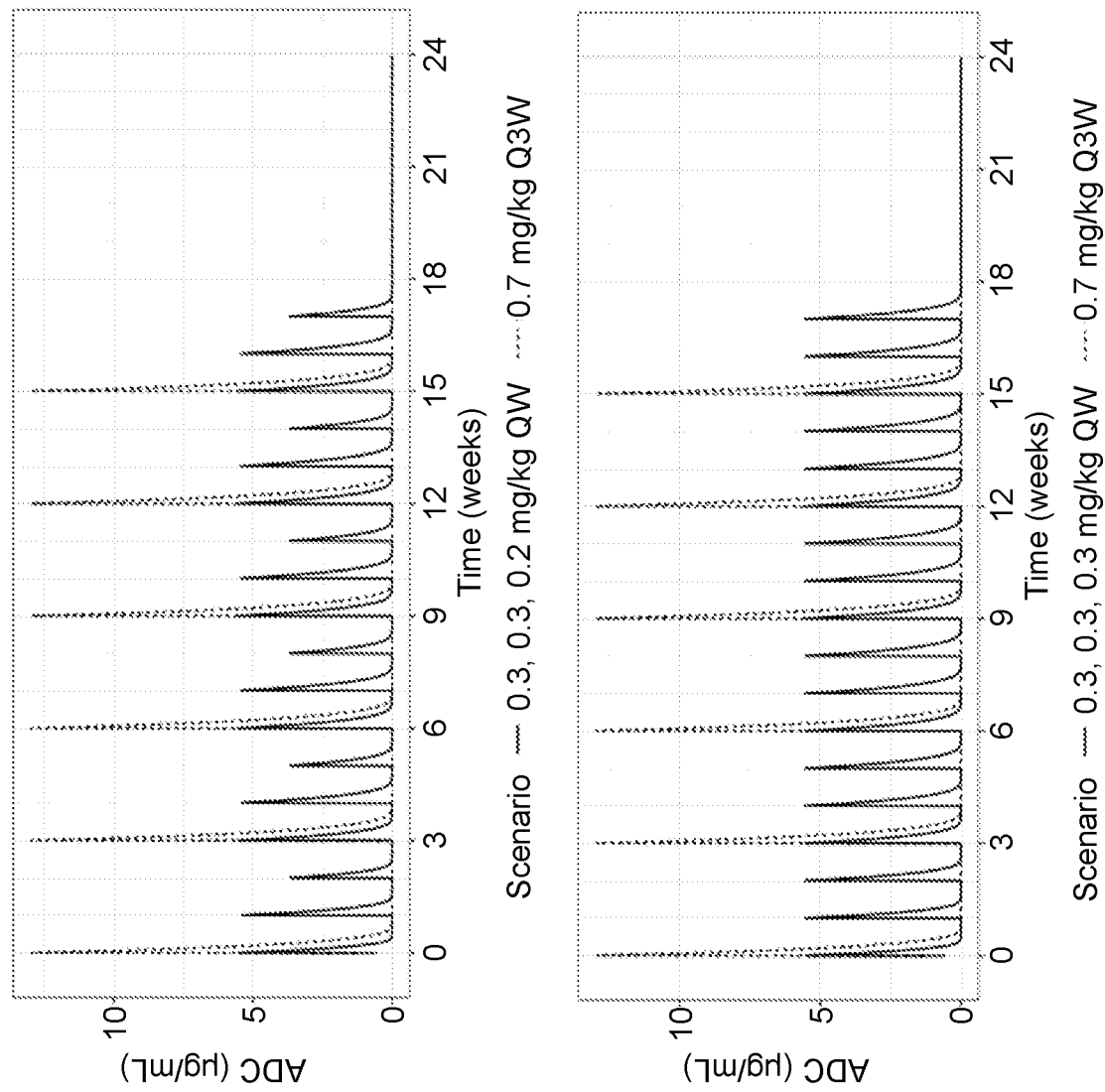

FIG. 2 shows simulations of Debio 1562 ("ADC") blood concentration in patients as a result of administration of three weekly doses of 0.3, 0.3, and 0.2 mg/kg, respectively, for six cycles as compared to administration of 0.7 mg/kg once every three weeks for six cycles (top panel) or administration of three weekly doses of 0.3 mg/kg for six cycles as compared to administration of 0.7 mg/kg once every three weeks for six cycles (bottom panel).

Figure 3:
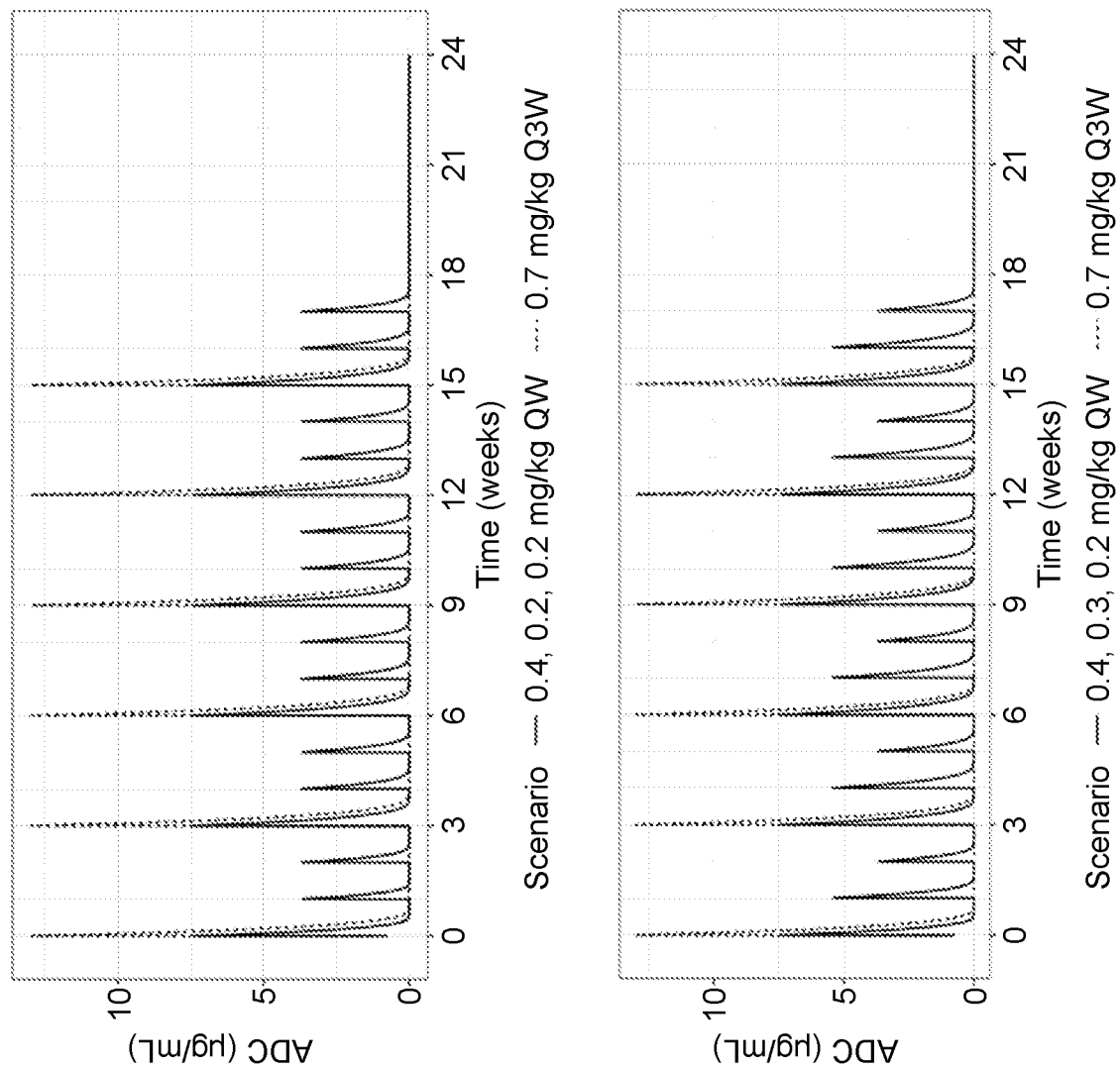

FIG. 3 shows simulations of Debio 1562 ("ADC") blood concentration in patients as a result of administration of three weekly doses of 0.4, 0.2, and 0.2 mg/kg, respectively, for six cycles as compared to administration of 0.7 mg/kg once every three weeks for six cycles (top panel) or administration of three weekly doses of 0.4, 0.3, and 0.2 mg/kg, respectively, for six cycles as compared to administration of 0.7 mg/kg once every three weeks for six cycles (bottom panel).

Figure 4:
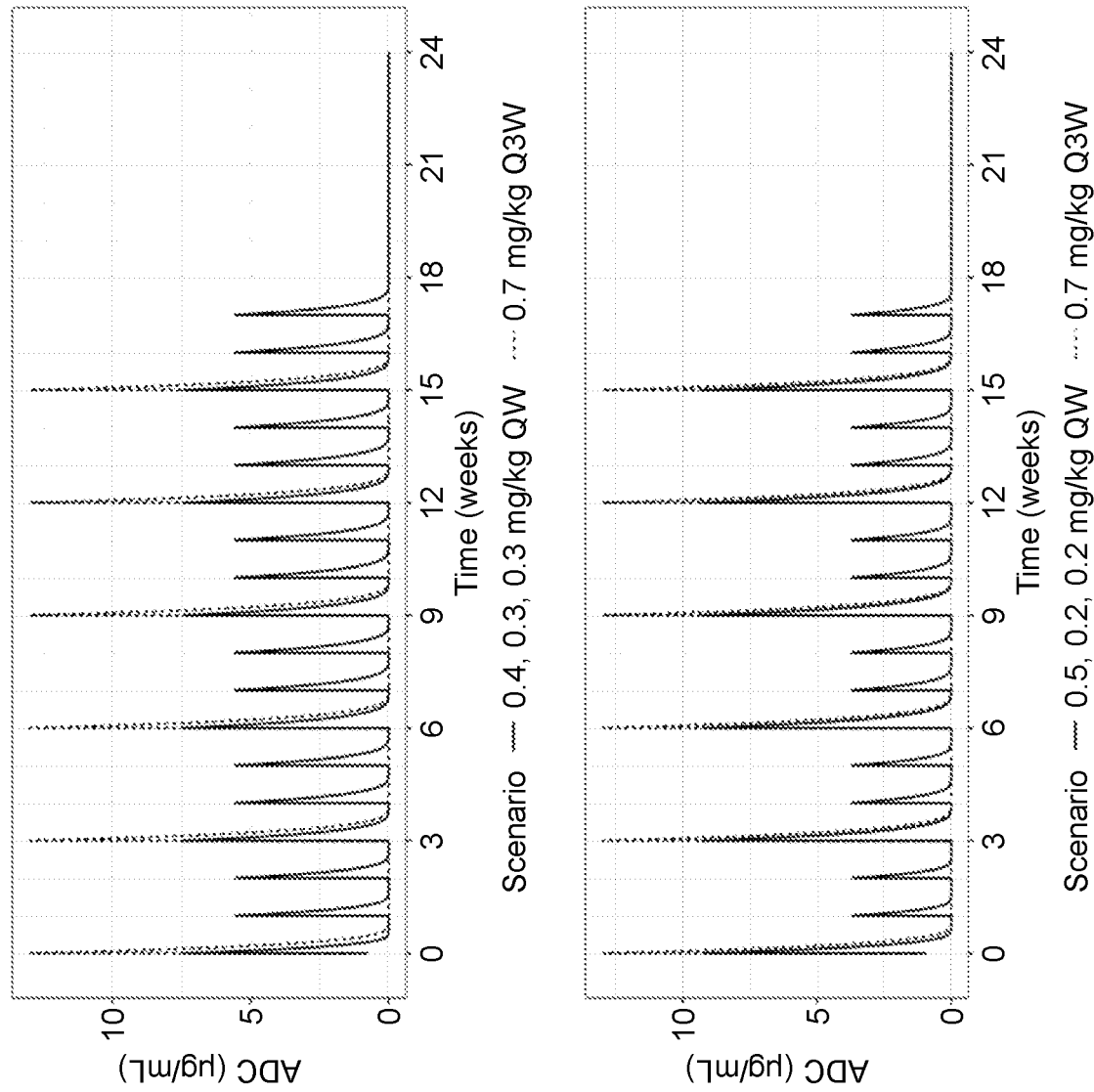

FIG. 4 shows simulations of Debio 1562 ("ADC") blood concentration in patients as a result of administration of three weekly doses of 0.4, 0.3, and 0.3 mg/kg, respectively, for six cycles as compared to administration of 0.7 mg/kg once every three weeks for six cycles (top panel) or administration of three weekly doses of 0.5, 0.2, and 0.2 mg/kg, respectively, for six cycles as compared to administration of 0.7 mg/kg once every three weeks for six cycles (bottom panel).

Figure 5:
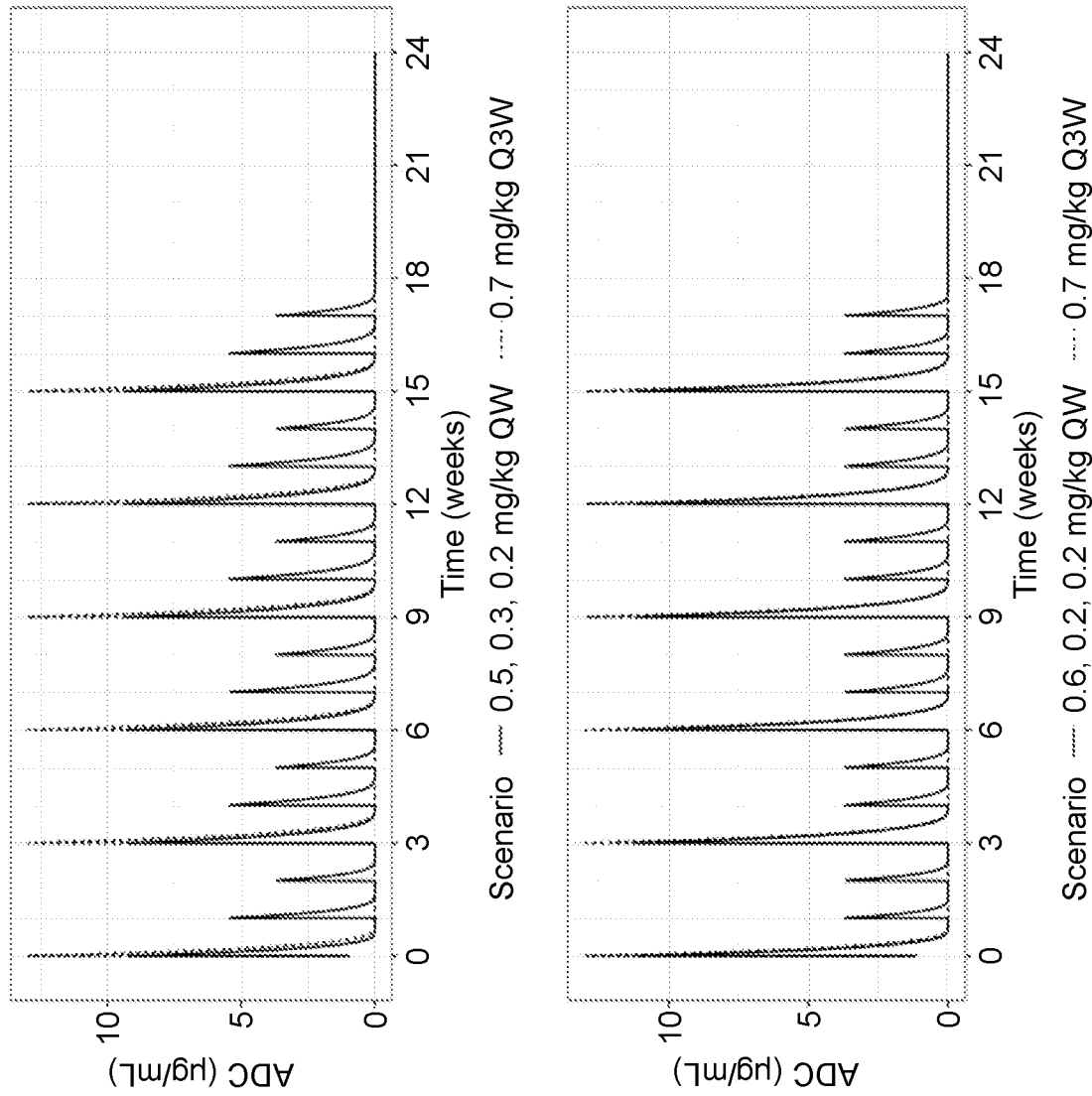

FIG. 5 shows simulations of Debio 1562 ("ADC") blood concentration in patients as a result of administration of three weekly doses of 0.5, 0.3, and 0.2 mg/kg, respectively, for six cycles as compared to administration of 0.7 mg/kg once every three weeks for six cycles (top panel) or administration of three weekly doses of 0.6, 0.2, and 0.2 mg/kg, respectively, for six cycles as compared to administration of 0.7 mg/kg once every three weeks for six cycles (bottom panel).

Figure 6:
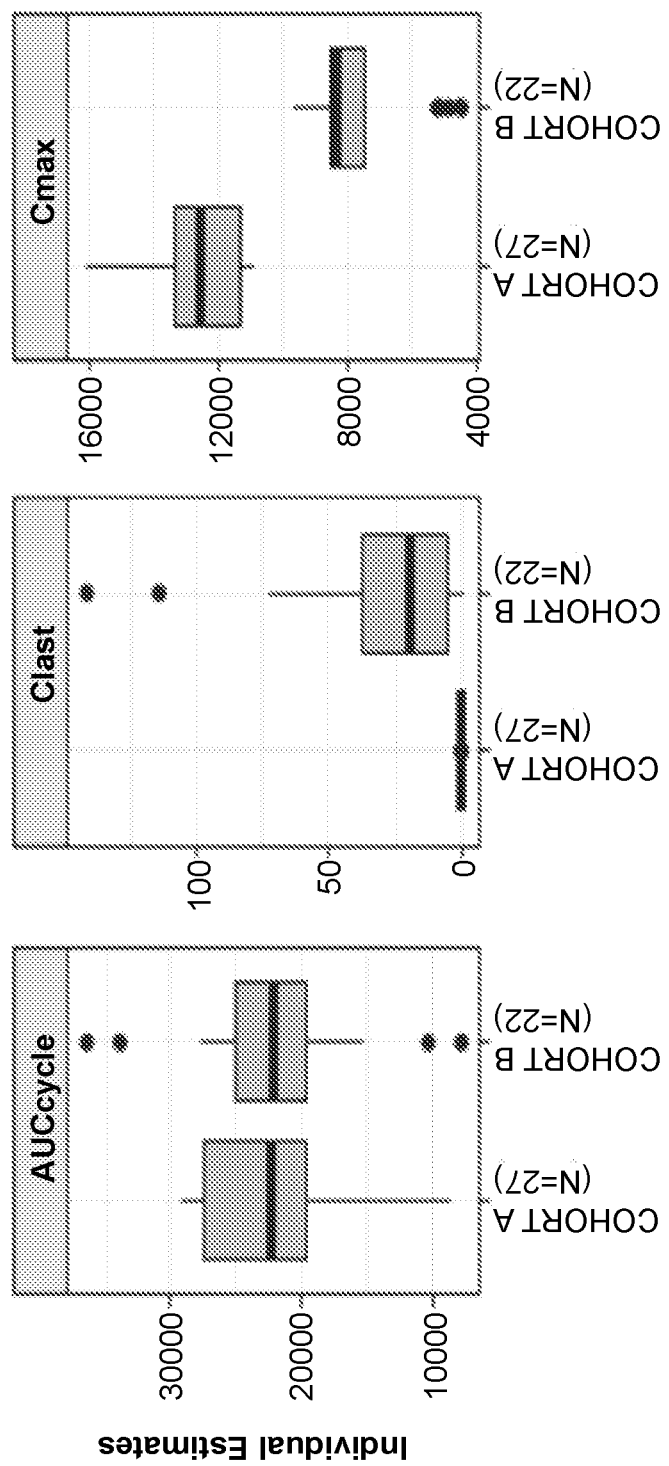

FIG. 6 shows pharmacokinetic parameters reflecting patient exposure to Debio 1562 in Cohort A (Q3W—once per 3 weeks regimen) and in Cohort B (QW—weekly administration in 3 weeks regimen). $AUC_{cycle}$=Area Under the Curve during a cycle of 3 weeks; $C_{last}$=last concentration measured during a cycle before the next Debio 1562 administration; $C_{max}$=maximal concentration observed per cycle; N represents the number of observations used to build the corresponding box plot—multiple values might be observed per subject. Box plots represent the median value and the $25^{th}$-$75^{th}$ percentiles.

Figure 7:
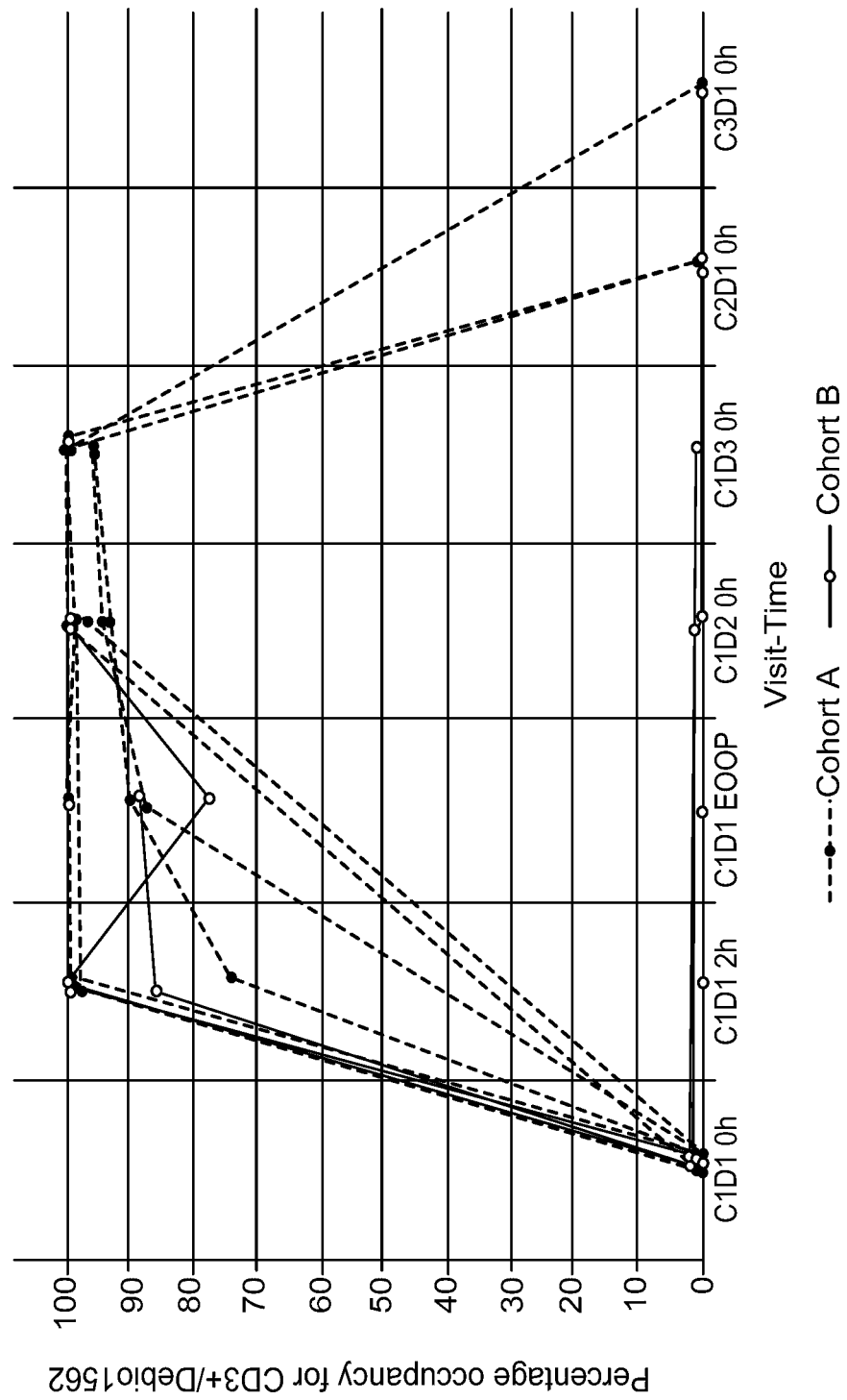

FIG. 7 shows the percentage of CD37 receptor occupancy (RO) on CD3+ T cells measured in Cohort A (Q3W) and in Cohort B (QW).

Figure 8:
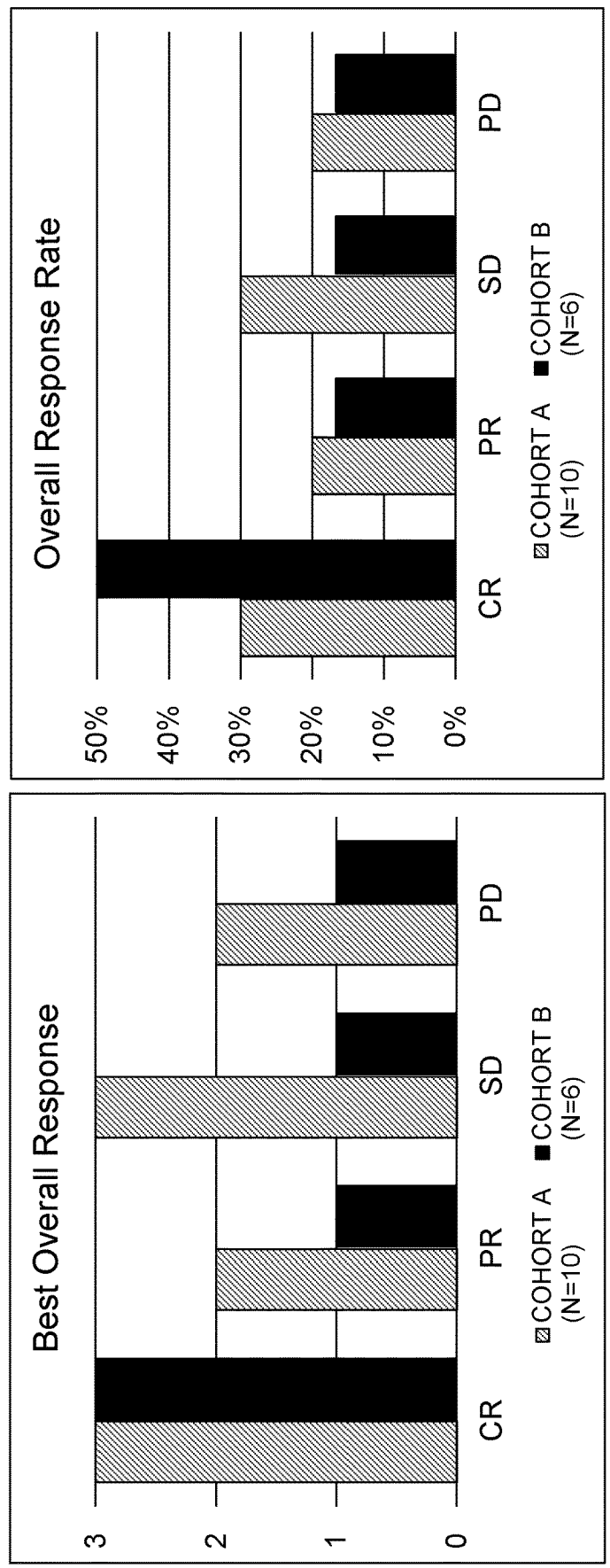

FIG. 8 shows categorical plots of best overall response (BOR) and overall response rate (ORR) as per 2014 Lugano classification in the Q3W regimen (Cohort A in light grey) and in the QW regimen (Cohort B in dark gray). Left panel shows data as number of patients per category. Right panel shows data as percentage of patients in each category relative to the total number of evaluable patients in the corresponding cohort. This plot is based on the data in 10 patients in Cohort A and 6 patients in Cohort B.

DETAILED DESCRIPTION OF THE INVENTION

The present invention provides new dosing regimens for CD37 binding immunoconjugates.

I. Definitions

To facilitate an understanding of the present invention, a number of terms and phrases are defined below.

The term "CD37" as used herein, refers to any native CD37, unless otherwise indicated. CD37 is also referred to as GP52-40, leukocyte antigen CD37, and Tetraspanin-26. The term "CD37" encompasses "full-length," unprocessed CD37 as well as any form of CD37 that results from processing in the cell. The term also encompasses naturally occurring variants of CD37, e.g., splice variants, allelic variants, and isoforms. The CD37 polypeptides described herein can be isolated from a variety of sources, such as from human tissue types or from another source, or prepared by recombinant or synthetic methods.

The term "CD20" as used herein, refers to any native CD20 polypeptide, unless otherwise indicated. CD20 is also referred to as membrane-spanning 4-domains, subfamily A, member 1 (MS4A1), B-lymphocyte surface antigen B1, and Leukocyte surface antigen Leu-16. The term "CD20" encompasses "full-length," unprocessed CD20 polypeptide as well as any form or isoform of CD20 polypeptide that results from processing in the cell. The term also encompasses naturally occurring variants of CD20 polypeptide, e.g., those encoded by splice variants and allelic variants. The CD20 polypeptides described herein can be isolated from a variety of sources, such as from human tissue types or from another source, or prepared by recombinant or synthetic methods. Where specifically indicated, "CD20" can be used to refer to a nucleic acid that encodes a CD20 protein.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain the antigenic determining regions of an intact antibody (e.g., the complementarity determining regions (CDR)). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

The term "anti-CD37 antibody" or "an antibody that binds to CD37" refers to an antibody that is capable of binding CD37 with sufficient affinity such that the antibody is useful as a diagnostic and/or therapeutic agent in targeting CD37. The extent of binding of an anti-CD37 antibody to an unrelated, non-CD37 protein can be less than about 10% of the binding of the antibody to CD37 as measured, e.g., by a radioimmunoassay (RIA). In certain embodiments, an antibody that binds to CD37 has a dissociation constant (Kd) of ≤1 µM, ≤100 nM, ≤10 nM, ≤1 nM, or ≤0.1 nM. Similarly, the term "anti-CD20 antibody" or "an antibody that binds to CD20" refers to an antibody that is capable of binding CD20 with sufficient affinity such that the antibody is useful as a diagnostic and/or therapeutic agent in targeting CD20. The extent of binding of an anti-CD20 antibody to an unrelated, non-CD20 protein can be less than about 10% of the binding of the antibody to CD20 as measured, e.g., by a radioimmunoassay (RIA). In certain embodiments, an antibody that binds to CD20 has a dissociation constant (Kd) of ≤1 µM, ≤100 nM, ≤10 nM, ≤1 nM, or ≤0.1 nM.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody refers to such antibodies made in any number of manners including but not limited to by hybridoma, phage selection, recombinant expression, and transgenic animals.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha (α), delta (δ), epsilon (ε), gamma (γ), and mu (µ), based on the amino acid sequence of the constant domain, which give rise to IgA, IgD, IgE, IgG, and IgM classes of antibodies, respectively, including subclasses of IgG, e.g., IgG$_1$, IgG$_2$, IgG$_3$, and IgG$_4$. Heavy chain amino acid sequences are well known in the art. In specific embodiments, the heavy chain is a human heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In certain instances, a "humanized antibody" is a resurfaced antibody.

The term "human" antibody or antigen-binding fragment thereof means an antibody or antigen-binding fragment thereof having an amino acid sequence derived from a human immunoglobulin gene locus, where such antibody or antigen-binding fragment is made using any technique known in the art. This definition of a human antibody or antigen-binding fragment thereof includes intact or full-length antibodies and fragments thereof.

The term "biosimilar" as used herein refers to a biological medicine highly similar to another biological medicine in terms of structure, biological activity and efficacy, safety and immunogenicity profile.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In certain instances, an antibody, polynucleotide, vector, cell, or composition which is isolated is substantially pure.

As used herein, "substantially pure" refers to material which is at least 50% pure (i.e., free from contaminants), at least 60% pure, at least 70% pure, at least 80% pure, at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-CD37 antibody or fragment thereof) and is defined by a generic formula: C-L-A, wherein C=cytotoxin, L=linker, and A=anti-CD37 antibody or antibody fragment. Immunoconjugates can also be defined by the generic formula in reverse order: A-L-C.

The term "Debio 1562" refers to the immunoconjugate described herein containing the huCD37-3 antibody (comprising the CDRs represented by SEQ ID NOs:2-7, the VH of SEQ ID NO:8 and the VL of SEQ ID NO:10), the SMCC linker, and the DM1 maytansinoid. It is also known as naratuximab emtansine and was previously known as IMGN529.

A "linker" is any chemical moiety that is capable of linking a compound, usually a drug, such as a maytansinoid, to a cell-binding agent such as an anti CD37 antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. "Tumor" and "neoplasm" refer to one or more cells that result from excessive cell growth or proliferation, either benign (noncancerous) or malignant (cancerous) including pre-cancerous lesions. Examples of "cancer" or "tumorigenic" diseases which can be treated and/or prevented include B-cell lymphomas including NHL, precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody or immunoconjugate as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size or burden; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP) or any combination thereof. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "respond favorably" generally refers to causing a beneficial state in a subject. With respect to cancer treatment, the term refers to providing a therapeutic effect on the subject. Positive therapeutic effects in cancer can be measured in a number of ways (See, W. A. Weber, J. Nucl. Med. 50:1S-10S (2009)). For example, tumor growth inhibition, molecular marker expression, serum marker expression, and molecular imaging techniques can all be used to assess therapeutic efficacy of an anti-cancer therapeutic. A favorable response can be assessed in the clinic, for example, by increased progression-free survival (PFS), disease-free survival (DFS), or overall survival (OS), complete response (CR), partial response (PR), or, in some cases, stable disease (SD), a decrease in progressive disease (PD), a reduced time to progression (TTP) or any combination thereof.

PFS, DFS, DoR, and OS can be measured by standards set by the National Cancer Institute and the U.S. Food and Drug Administration for the approval of new drugs. See Johnson et al, (2003) J. Clin. Oncol. 21(7): 1404-1411.

"Progression free survival" (PFS) refers to the time from enrollment to disease progression or death. PFS is generally summarized using the Kaplan-Meier method. Generally, progression free survival refers to the situation wherein a patient remains alive, without the cancer getting worse.

"Time to Tumor Progression" (TTP) is defined as the time from enrollment to disease progression. TTP is generally measured using the RECIST 1.1 criteria.

A "complete response" or "complete remission" or "CR" indicates the disappearance of all signs of tumor or cancer in response to treatment. This does not always mean the cancer has been cured. For example, any pathological lymph nodes (whether target or non-target) must have reduction in the short axis to <10 mm. Complete response in solid tumors is generally measured using the RECIST 1.1 criteria. Eisenhauer, E. A., Eur. J. Cancer, 45: 228-47 (2009). Complete response in NHL is generally measured using the Lugano classification. Cheson, B. D et al., J Clin Oncol., 32: 3059-3067 (2014). Other tumor response criteria may also be used as appropriate for the relevant indication.

A "partial response" or "PR" refers to a decrease in the size or volume of one or more tumors or lesions, or in the extent of cancer in the body, in response to treatment. Eisenhauer, E. A., Eur. J. Cancer, 45: 228-47 (2009). Cheson, B. D et al., J Clin Oncol., 32: 3059-3067 (2014).

"Stable disease" or "SD" refers to disease without progression or relapse. In stable disease there is neither sufficient tumor shrinkage to qualify for partial response nor sufficient tumor increase to qualify as progressive disease taking as reference the smallest sum diameters while on the study. Eisenhauer, E. A., Eur. J. Cancer, 45: 228-47 (2009). Cheson, B. D et al., J Clin Oncol., 32: 3059-3067 (2014).

"Progressive disease" or "PD" refers to the appearance of one more new lesions or tumors and/or the unequivocal progression of existing non-target lesions and/or at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). Eisenhauer, E. A., Eur. J. Cancer, 45: 228-47 (2009). Cheson, B. D et al., J Clin Oncol., 32: 3059-3067 (2014).

"Disease free survival" (DFS) refers to the length of time during and after treatment that the patient remains free of disease.

"Duration of response" (DoR) refers to the time from earlier response (PR or better) to disease progression or death.

"Overall Survival" (OS) refers to the time from patient enrollment to death or censored at the date last known alive. OS includes a prolongation in life expectancy as compared to naive or untreated individuals or patients. Overall survival refers to the situation wherein a patient remains alive for a defined period of time, such as one year, five years, etc., e.g., from the time of randomization or treatment.

The term "overexpression" of CD37 in a particular tumor, tissue, or cell sample refers to CD37 (a CD37 polypeptide or a nucleic acid encoding such a polypeptide) that is present at a level higher than that which is present in non-diseased tissue or cells of the same type or origin. Such overexpression can be caused, for example, by mutation, gene amplification, increased transcription, or increased translation.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor burden; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

The terms "pre-treat" and "pre-treatment" refer to therapeutic measures that occur prior to the administration of an anti-CD37 therapeutic. For example, as described in more detail herein, a prophylactic such as a steroid (e.g., corticosteroid) can be administered within about a week, about five days, about three days, about two days, or about one day or 24 hours prior to the administration of the anti-CD37 therapeutic. The prophylactic can also be administered prior to the anti-CD37 therapeutic on the same day as the anti-CD37 therapeutic.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Anti-CD37 Immunoconjugates

The methods described herein provide methods of administering immunoconjugates that specifically bind to CD37. These agents are referred to herein as "CD37-immunoconjugates" or "anti-CD37-immunoconjugates." Such immunoconjugates comprise an anti-CD37 antibody or antigen-binding fragment thereof and a drug (e.g., a maytansinoid). The drug (e.g., a maytansinoid) can be attached to the anti-CD37 antibody or antigen-binding fragment thereof by a linker (e.g., an SMCC linker). An immunoconjugate can contain multiple drugs (e.g., 1-10 maytansinoids), wherein each drug (e.g., maytansinoid) can be linked to the antibody or antigen-binding fragment thereof by a linker (e.g., an SMCC linker).

The anti-CD37 immunoconjugate can bind, for example, to human CD37. The full-length amino acid sequence for human CD37 is known in the art (NP_001765.1) and is also provided herein as SEQ ID NO:1. MSAQESCLSLIKYFLFVFNLFFFVLGSLIFCFGIWILIDKTSFVSFVGLAFVPLQIWS KVLAISGIFTMGIALLGCVGALKELRCLLGLYFGMLLLLFATQITLGILISTQRAQL ERSLRDVVEKTIQKYGTNPEETAAEESWDYVQFQLRCCGWHYPQDWFQVLILRG NGSEAHR VPCSCYNLSATNDSTILDKVILPQLSRLGHLARSRHSADICAVPAESHI YREGCAQGLQKWLHNNLISIVGICLGVGLLELGFMTLSIFLCRNLDHVYNRLAYR (SEQ ID NO:1)

In certain instances, the anti-CD37 immunoconjugates (e.g., Debio 1562) have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells. In certain instances, the anti-CD37 immunoconjugates (e.g., Debio 1562) trigger cell death via a cytotoxic agent. In certain instances, the anti-CD37 immunoconjugates (e.g., Debio 1562) are capable of inhibiting tumor growth. In certain instances, the anti-CD37 immunoconjugates (e.g., Debio 1562) are capable of inhibiting tumor growth in vivo (e.g., in a xenograft mouse model and/or in a human having cancer). The anti-CD37 immunoconjugates (e.g., Debio 1562) can comprise the antibody huCD37-3 or fragments, variants and derivatives thereof, as described previously in U.S. Publication No. 2011/0256153, which is herein incorporated by reference in its entirety.

In some instances, an anti-CD37 immunoconjugate comprises a humanized anti-CD37 antibody or antigen-binding fragment thereof.

In some instances, an anti-CD37 immunoconjugate (e.g., Debio 1562) comprises the heavy chain and light chain variable region CDR sequences of the humanized anti-CD37-3 antibodies ("huCD37-3"). The CDR sequences of huCD37-3 are provided in Tables 1 and 2 below.

TABLE 1

Variable heavy chain CDR amino acid sequences

| Antibody | VH-CDR1 | VH-CDR2 | VH-CDR3 |
|---|---|---|---|
| CD37-3 | TSGVS (SEQ ID NO: 2) | VIWGDGSTN (SEQ ID NO: 3) | GGYSLAH (SEQ ID NO: 4) |

TABLE 2

Variable light chain CDR amino acid sequences

| Antibody | VL-CDR1 | VL-CDR2 | VL-CDR3 |
|---|---|---|---|
| CD37-3 | RASENIRSNLA (SEQ ID NO: 5) | VATNLAD (SEQ ID NO: 6) | QHYWGTTWT (SEQ ID NO: 7) |

In some instances, an anti-CD37 immunoconjugate (e.g., Debio 1562) comprises an antibody or antigen-binding fragment thereof comprising variable heavy chain CDR1, CDR2, and CDR3 sequences comprising SEQ ID NOs: 2, 3, and 4, respectively, and variable light chain CDR1, CDR2, and CDR3 sequences comprising SEQ ID NOs: 5, 6, and 7 respectively.

In some instances, an anti-CD37 immunoconjugate (e.g., Debio 1562) comprises a variable light chain or a variable heavy chain described herein. In some instances, an anti-CD37 immunoconjugate (e.g., Debio 1562) comprises both a variable light chain and a variable heavy chain provided herein. The variable light chain and variable heavy chain sequences of huCD37-3 antibodies (version 1.0 and version 1.1) are provided in Tables 3 and 4 below.

TABLE 3

Variable heavy chain amino acid sequences

| Antibody | VH Amino Acid Sequence (SEQ ID NO) |
|---|---|
| huCD37-3 (version 1.0) | QVQVQESGPGLVAPSQTLSITCTVSGFSLTTSGV SWVRQPPGKGLEWLGVIWGDGSTNYHPSLKSRLS IKKDHSKSQVFLKLNSLTAADTATYYCAKGGYSL AHWGQGTLVTVSS (SEQ ID NO: 8) |
| huCD37-3 (version 1.1) | QVQVQESGPGLVAPSQTLSITCTVSGFSLTTSGV SWVRQPPGKGLEWLGVIWGDGSTNYHSSLKSRLS IKKDHSKSQVFLKLNSLTAADTATYYCAKGGYSL AHWGQGTLVTVSS (SEQ ID NO: 9) |

TABLE 4

Variable light chain amino acid sequence

| Antibody | VL Amino Acid Sequence (SEQ ID NO) |
|---|---|
| huCD37-3 | DIQMTQSPSSLSVSVGERVTITCRASENIRSNLAWYQQK PGKSPKLLVNVATNLADGVPSRFSGSGSGTDYSLKINSL QPEDFGTYYCQHYWGTTWTFGQGTKLEIKR (SEQ ID NO: 10) |

An anti-CD37 immunoconjugate (e.g., Debio 1562) can also comprise a full-length light chain or a full-length heavy chain. In certain instances, an anti-CD37 immunoconjugate (e.g., Debio 1562) can comprise both a full-length light chain and a full-length heavy chain. The full-length light chain and heavy chain sequences of huCD37-3 (version 1.0) are provided in Tables 5 and 6 below.

TABLE 5

Full-length heavy chain amino acid sequence

| Antibody | Full-Length Heavy Chain Amino Acid Sequence (SEQ ID NO) |
|---|---|
| huCD37-3 (version 1.0) | QVQVQESGPGLVAPSQTLSITCTVSGFSLTTSGV SWVRQPPGKGLEWLGVIWGDGSTNYHPSLKSRLS IKKDHSKSQVFLKLNSLTAADTATYYCAKGGYSL AHWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKP SNTKVDKKVEPKSCDKTHTCPPCPAPELLGGPSV FLFPPKPKDTLMISRTPEVTCVVVDVSHEDPEVK FNWYVDGVEVHNAKTKPREEQYNSTYRVVSVLTV LHQDWLNGKEYKCKVSNKALPAPIEKTISKAKGQ PREPQVYTLPPSRDELTKNQVSLTCLVKGFYPSD IAVEWESNGQPENNYKTTPPVLDSDGSFFLYSKL TVDKSRWQQGNVFSCSVMHEALHNHYTQKSLSLS PG (SEQ ID NO: 11) |

TABLE 6

Full-length light chain amino acid sequence

| Antibody | Full-length Light Chain Amino Acid Sequence (SEQ ID NO) |
|---|---|
| huCD37-3 | DIQMTQSPSSLSVSVGERVTITCRASENIRSNLAWYQQK PGKSPKLLVNVATNLADGVPSRFSGSGSGTDYSLKINSL |

TABLE 6-continued

Full-length light chain amino acid sequence

| Antibody | Full-length Light Chain Amino Acid Sequence (SEQ ID NO) |
|---|---|
| | QPEDFGTYYCQHYWGTTWTFGQGTKLEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC (SEQ ID NO: 12) |

In certain instances, the anti-CD37 immunoconjugate (e.g., Debio 1562) can comprise an anti-CD37 antibody or antigen-binding fragment thereof comprising a light chain or light chain variable region having the same amino acid sequence as the amino acid sequence encoded by the recombinant plasmid DNA phuCD37-3LC (ATCC Deposit Designation PTA-10722, deposited with the ATCC on Mar. 18, 2010). In certain instances, the anti-CD37 antibody or antigen-binding fragment thereof can comprise a heavy chain or heavy chain variable region comprising the same amino acid sequence as the amino acid sequence encoded by the recombinant plasmid DNA phuCD37-3HCv.1.0 (ATCC Deposit Designation PTA-10723, deposited with the ATCC on Mar. 18, 2010). In certain instances, the anti-CD37 antibody or antigen-binding fragment thereof can comprise a light chain or light chain variable region comprising the same amino acid sequence as the amino acid sequence encoded by the recombinant plasmid DNA phuCD37-3LC (PTA-10722) and a heavy chain or heavy chain variable region comprising the same amino acid sequence as the amino acid sequence encoded by the recombinant plasmid DNA phuCD37-3HCv.1.0 (PTA-10723). In certain instances, the anti-CD37 antibody or antigen-binding fragment thereof can comprise (i) VL-CDRs comprising the same amino acid sequences as the VL-CDRs encoded by the recombinant plasmid DNA phuCD37-3LC (PTA-10722) and (ii) VH-CDRs comprising the same amino acid sequences as the VH-CDRs encoded by the recombinant plasmid DNA phuCD37-3HCv.1.0 (PTA-10723).

As provided herein, in certain instances, about 1 to about 8 drug molecules e.g., maytansinoids, are linked to an anti-CD37 antibody or antigen-binding fragment thereof. In one aspect, an immunoconjugate comprises 1, 2, 3, 4, 5, 6, 7, or 8 maytansinoids per antibody or antigen-binding fragment thereof. In one aspect, an immunoconjugate comprises about 1 to about 8 maytansinoids per antibody or antigen-binding fragment thereof, about 2 to about 7 maytansinoids per antibody or antigen-binding fragment thereof, about 2 to about 6 maytansinoids per antibody or antigen-binding fragment thereof, about 2 to about 5 maytansinoids per antibody or antigen-binding fragment thereof, about 3 to about 5 maytansinoids per antibody or antigen-binding fragment thereof, or about 3 to about 4 maytansinoids per antibody or antigen-binding fragment thereof.

In certain instances a composition provided herein comprises anti-CD37 immunoconjugates comprising about 1 to about 10 maytansinoids per antibody or antigen-binding fragment thereof, for example, wherein the average number of maytansinoids per antibody or antigen-binding fragment thereof is from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1).

In certain instances, a composition provided herein comprises anti-CD37 immunoconjugates with an average of about 2±0.5, about 3±0.5, about 4±0.5, about 5±0.5, about 6±0.5, about 7±0.5, or about 8±0.5 drug molecules (e.g., maytansinoids) attached per antibody or antigen-binding fragment thereof. In certain aspects, a composition provided herein comprises anti-CD37 immunoconjugates with an average of about 3.5±0.5 drug molecules (e.g., maytansinoids) per antibody. In certain aspects, a composition provided herein comprises anti-CD37 immunoconjugates with an average of 3.5±0.5 drug molecules (e.g., maytansinoids) per antibody.

As used herein, the expression "linked to a cell-binding agent" or "linked to an anti-CD37 antibody or fragment" refers to the conjugate molecule comprising at least one drug derivative bound to a cell-binding agent anti-CD37 antibody or fragment via a suitable linking group, or a precursor thereof. One linking group is SMCC.

Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain instance, the immunoconjugates of the invention utilize the thiol-containing maytansinoid (DM1), formally termed $N^{2'}$-deacetyl-$N^{2'}$-(3-mercapto-1-oxopropy 1)-maytansine, as the cytotoxic agent. DM1 is represented by the following structural formula (I):

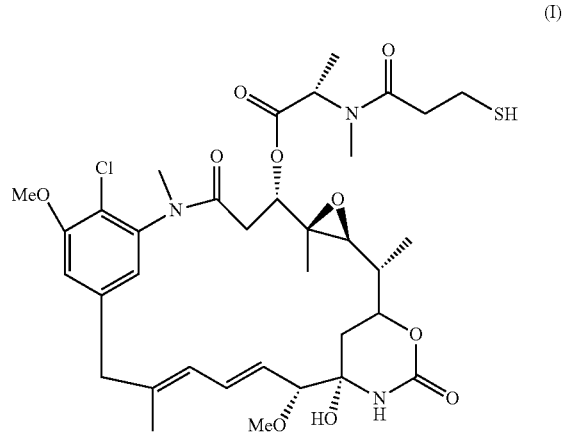 [SMILES: COc1cc2cc(c1Cl)N(C)C(=O)C[C@H](OC(=O)[C@H](C)N(C)C(=O)CCS)[C@]1(C)O[C@H]1[C@H](C)C1C[C@@](O)(NC(=O)O1)[C@H](OC)/C=C/C=C(\C)C2]

(I)

In another instance, the conjugates of the present invention utilize the thiol-containing maytansinoid $N^{2'}$-deacetyl-$N^{2'}$ (4-methyl-4-mercapto-1-oxopentyl)-maytansine (e.g., DM4) as the cytotoxic agent. DM4 is represented by the following structural formula (II):

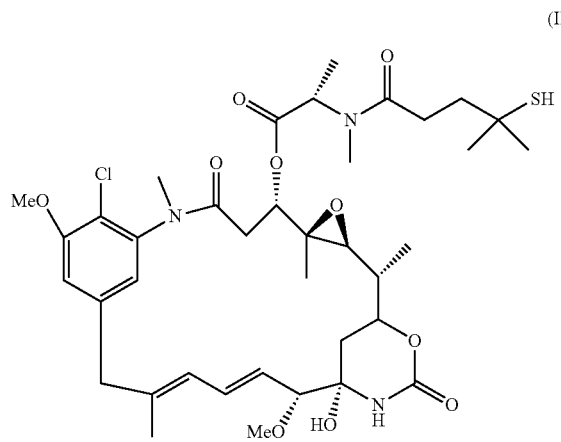

(II)

Another maytansinoid comprising a side chain that contains a sterically hindered thiol bond is N$^{2'}$-deacetyl-N-$^{2'}$-(4-mercapto-1-oxopentyl)-maytansine (termed DM3), represented by the following structural formula (III):

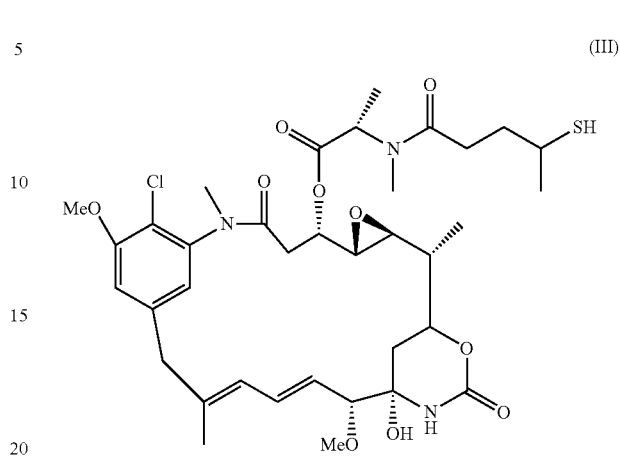

(III)

Structural representations of some conjugates are shown below:

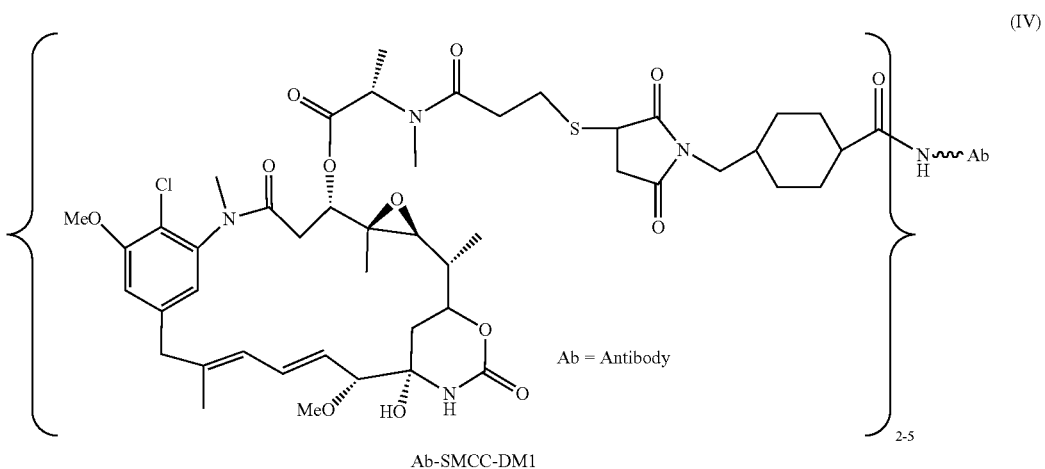

(IV)

Ab-SMCC-DM1

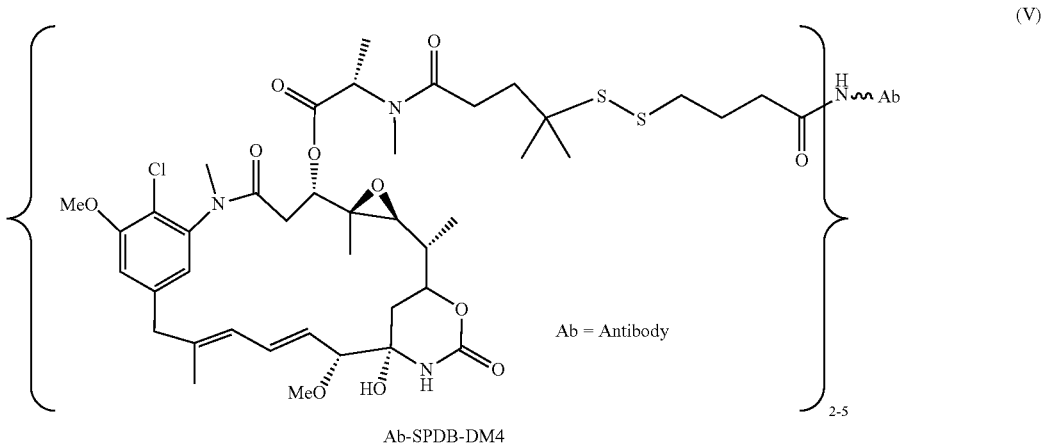

(V)

Ab-SPDB-DM4

-continued (VI)

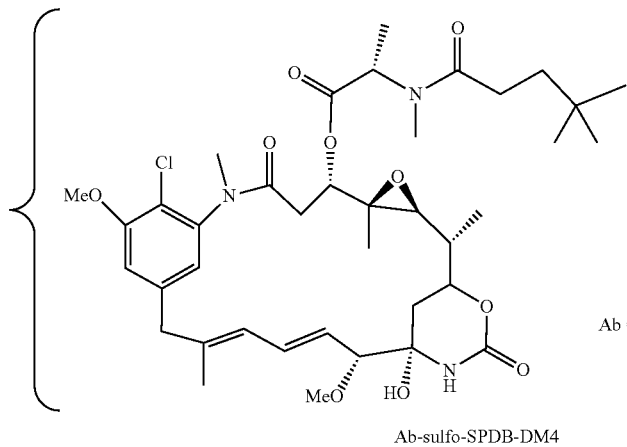
Ab-sulfo-SPDB-DM4

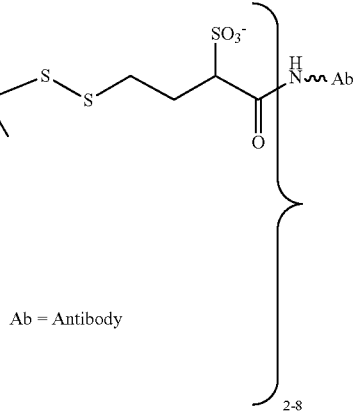
Ab = Antibody

Also included in the present invention are any stereoisomers and mixtures thereof for any compounds or conjugates depicted by any structures above.

The maytansinoid can be, e.g., $N^{2'}$-deacetyl-$N^{2'}$-(3-mercapto-1-oxopropyl)-maytansine (DM1).

The immunoconjugates can, according to some instances described herein, be internalized into cells. The immunoconjugate, therefore, can exert a therapeutic effect when it is taken up by, or internalized, by a CD37-expressing cell.

III. Anti-CD20 Therapy

In certain instances, the methods described herein comprise administering an anti-CD37 immunoconjugate (e.g., Debio 1562) in combination with an anti-CD20 therapy.

In certain instances, the anti-CD20 therapy is rituximab, an antigen-binding fragment thereof, or a biosimilar thereof. In certain instances, the anti-CD20 therapy is ofatumumab, an antigen-binding fragment thereof, or a biosimilar thereof. In certain instances, the anti-CD20 therapy is obinutuzumab, an antigen-binding fragment thereof, or a biosimilar thereof. In certain instances, the anti-CD20 therapy is veltuzumab an antigen-binding fragment thereof, or a biosimilar thereof.

In certain instances, the methods described herein comprise administering an anti-CD37 immunoconjugate (e.g., Debio 1562) in combination with rituximab. Rituximab is an anti-CD20 antibody marketed as Rituxan®. The variable heavy and variable light chain amino acid sequences of rituximab are provided in Table 7.

TABLE 7

| Rituximab variable heavy chain and variable light chain amino acid sequences | |
|---|---|
| Rituximab variable heavy chain | QVQLQQPGAELVKPGASVKMSCKASGYTF TSYNMHWVKQTPGRGLEWIGAIYPGNGDT SYNQKFKGKATLTADKSSSTAYMQLSSLT SEDSAVYYCARSTYYGGDWYFNVWGAGTT VTVSA (SEQ ID NO: 13) |
| Rituximab variable light chain | QIVLSQSPAILSASPGEKVTMTCRASSSV SYIHWFQQKPGSSPKPWIYATSNLASGVP VRFSGSGSGTSYSLTISRVEAEDAATYYC QQWTSNPPTFGGGTKLEIK (SEQ ID NO: 14) |

As used herein, the administration of rituximab "in combination" with an anti-CD37 immunoconjugate (e.g., Debio 1562) encompasses simultaneous or sequential administration of the rituximab and the anti-CD37 immunoconjugate (e.g., Debio 1562). In certain instances, the rituximab and the anti-CD37 immunoconjugate (e.g., Debio 1562) are administered sequentially in separate pharmaceutical compositions, e.g., with the rituximab being administered after the administration of the anti-CD37 immunoconjugate (e.g., Debio 1562) on the same day as the anti-CD37 immunoconjugate (e.g., Debio 1562) is administered.

Use of an anti-CD37 immunoconjugate (e.g., Debio 1562) in combination with rituximab can provide "synergy" and prove "synergistic", i.e., the effect achieved when the active ingredients used together is greater than the sum of the effects that results from using the compounds separately. This has been described in WO 2016/200676, which is herein incorporated by reference in its entirety. The combination of Debio 1562 and rituximab demonstrated synergistic pro-apoptotic activity in a panel of cell lines representative of diverse NHL subtypes, including activated B-cell like (ABC) and germinal center B-cell-like (GCB) DLBCL, CLL and MCL.

IV. Methods of Administering Pharmaceutical Compositions Comprising Anti-CD37 Immunoconjugates The present disclosure relates to a weekly dosage regimen for administering an anti-CD37 immunoconjugate (e.g. Debio 1562) (optionally in combination with an anti-CD20 therapy (e.g., rituximab)) to a human patient to treat cancer. The cancer can be, for example, a B-cell malignancy.

In certain instances, the anti-CD37 immunoconjugate (e.g., Debio 1562) is administered once a week in a three-week cycle, for example, on Day 1, Day 8, and Day 15 of a 21-day cycle. Weekly administration of the anti-CD37 immunoconjugate (e.g., Debio 1562) can maintain a constant and prolonged exposure of the CD37 antigen to Debio 1562. Weekly administration of the anti-CD37 immunoconjugate (e.g., Debio 1562) can also limit the risk of safety issue (e.g. neutropenia) while maintaining the saturation of CD37 antigens on target cells. Rituximab can also be administered, for example every three weeks (e.g., on Day 1 of the 21-day cycle after the anti-CD37 immunoconjugate (e.g., Debio 1562) is administered). Weekly administration of the anti-CD37 immunoconjugate (e.g., Debio 1562) in combination with rituximab can prolong the synergistic effect with rituximab. Rituximab can also be administered once every four weeks (one month), once every two months, or once every three months.

Patients can be treated for at least two three-week (21-day) cycles. Patients can be treated for at least three three-week (21-day) cycles. Patients can be treated for at least four three-week (21-day) cycles. Patients can be treated for at least five three-week (21-day) cycles. Patients can be treated for at least six three-week (21-day) cycles.

Patients can be treated for one to six three-week (21-day) cycles. Patients can be treated for two to six three-week (21-day) cycles. Patients can be treated for three to six three-week (21-day) cycles. Patients can be treated for four to six three-week (21-day) cycles. Patients can be treated for five to six three-week (21-day) cycles.

In certain instances, 0.2 mg/kg of the anti-CD37 immunoconjugate (e.g., Debio 1562) is administered in the first week (e.g., on Day 1), 0.2 mg/kg of the anti-CD37 immunoconjugate (e.g., Debio 1562) is administered in the second week (e.g., on Day 8), and 0.2 mg/kg of the anti-CD37 immunoconjugate (e.g., Debio 1562) is administered in the third week (e.g., on Day 15). Rituximab can also be administered in the first week (e.g., on Day 1 after administration of the anti-CD37 immunoconjugate (e.g., Debio 1562)), at a dose, for example, of 375 mg/m$^2$.

In certain instances, 0.3 mg/kg of the anti-CD37 immunoconjugate (e.g., Debio 1562) is administered in the first week (e.g., on Day 1), 0.3 mg/kg of the anti-CD37 immunoconjugate (e.g., Debio 1562) is administered in the second week (e.g., on Day 8), and 0.3 mg/kg of the anti-CD37 immunoconjugate (e.g., Debio 1562) is administered in the third week (e.g., on Day 15). Rituximab can also be administered in the first week (e.g., on Day 1 after administration of the anti-CD37 immunoconjugate (e.g., Debio 1562)), at a dose, for example, of 375 mg/m$^2$.

In certain instances, 0.3 mg/kg of the anti-CD37 immunoconjugate (e.g., Debio 1562) is administered in the first week (e.g., on Day 1), 0.3 mg/kg of the anti-CD37 immunoconjugate (e.g., Debio 1562) is administered in the second week (e.g., on Day 8), and 0.2 mg/kg of the anti-CD37 immunoconjugate (e.g., Debio 1562) is administered in the third week (e.g., on Day 15). Rituximab can also be administered in the first week (e.g., on Day 1 after administration of the anti-CD37 immunoconjugate (e.g., Debio 1562)), at a dose, for example, of 375 mg/m$^2$.

In certain instances, 0.3 mg/kg of the anti-CD37 immunoconjugate (e.g., Debio 1562) is administered in the first week (e.g., on Day 1), 0.2 mg/kg of the anti-CD37 immunoconjugate (e.g., Debio 1562) is administered in the second week (e.g., on Day 8), and 0.2 mg/kg of the anti-CD37 immunoconjugate (e.g., Debio 1562) is administered in the third week (e.g., on Day 15). Rituximab can also be administered in the first week (e.g., on Day 1 after administration of the anti-CD37 immunoconjugate (e.g., Debio 1562)), at a dose, for example, of 375 mg/m$^2$.

In certain instances, 0.4 mg/kg of the anti-CD37 immunoconjugate (e.g., Debio 1562) is administered in the first week (e.g., on Day 1), 0.3 mg/kg of the anti-CD37 immunoconjugate (e.g., Debio 1562) is administered in the second week (e.g., on Day 8), and 0.3 mg/kg of the anti-CD37 immunoconjugate (e.g., Debio 1562) is administered in the third week (e.g., on Day 15). Rituximab can also be administered in the first week (e.g., on Day 1 after administration of the anti-CD37 immunoconjugate (e.g., Debio 1562)), at a dose, for example, of 375 mg/m$^2$.

In certain instances, 0.4 mg/kg of the anti-CD37 immunoconjugate (e.g., Debio 1562) is administered in the first week (e.g., on Day 1), 0.3 mg/kg of the anti-CD37 immunoconjugate (e.g., Debio 1562) is administered in the second week (e.g., on Day 8), and 0.2 mg/kg of the anti-CD37 immunoconjugate (e.g., Debio 1562) is administered in the third week (e.g., on Day 15). Rituximab can also be administered in the first week (e.g., on Day 1 after administration of the anti-CD37 immunoconjugate (e.g., Debio 1562)), at a dose, for example, of 375 mg/m$^2$.

In certain instances, 0.4 mg/kg of the anti-CD37 immunoconjugate (e.g., Debio 1562) is administered in the first week (e.g., on Day 1), 0.2 mg/kg of the anti-CD37 immunoconjugate (e.g., Debio 1562) is administered in the second week (e.g., on Day 8), and 0.2 mg/kg of the anti-CD37 immunoconjugate (e.g., Debio 1562) is administered in the third week (e.g., on Day 15). Rituximab can also be administered in the first week (e.g., on Day 1 after administration of the anti-CD37 immunoconjugate (e.g., Debio 1562)), at a dose, for example, of 375 mg/m$^2$.

In certain instances, 0.5 mg/kg of the anti-CD37 immunoconjugate (e.g., Debio 1562) is administered in the first week (e.g., on Day 1), 0.3 mg/kg of the anti-CD37 immunoconjugate (e.g., Debio 1562) is administered in the second week (e.g., on Day 8), and 0.2 mg/kg of the anti-CD37 immunoconjugate (e.g., Debio 1562) is administered in the third week (e.g., on Day 15). Rituximab can also be administered in the first week (e.g., on Day 1 after administration of the anti-CD37 immunoconjugate (e.g., Debio 1562)), at a dose, for example, of 375 mg/m$^2$.

In certain instances, 0.5 mg/kg of the anti-CD37 immunoconjugate (e.g., Debio 1562) is administered in the first week (e.g., on Day 1), 0.2 mg/kg of the anti-CD37 immunoconjugate (e.g., Debio 1562) is administered in the second week (e.g., on Day 8), and 0.2 mg/kg of the anti-CD37 immunoconjugate (e.g., Debio 1562) is administered in the third week (e.g., on Day 15). Rituximab can also be administered in the first week (e.g., on Day 1 after administration of the anti-CD37 immunoconjugate (e.g., Debio 1562)), at a dose, for example, of 375 mg/m$^2$.

In certain instances, 0.6 mg/kg of the anti-CD37 immunoconjugate (e.g., Debio 1562) is administered in the first week (e.g., on Day 1), 0.2 mg/kg of the anti-CD37 immunoconjugate (e.g., Debio 1562) is administered in the second week (e.g., on Day 8), and 0.2 mg/kg of the anti-CD37 immunoconjugate (e.g., Debio 1562) is administered in the third week (e.g., on Day 15). Rituximab can also be administered in the first week (e.g., on Day 1 after administration of the anti-CD37 immunoconjugate (e.g., Debio 1562)), at a dose, for example, of 375 mg/m$^2$.

In certain instances, the anti-CD37 immunoconjugate (e.g., Debio 1562) is administered intravenously. In certain instances, the rituximab is administered intravenously. In certain instances, both the anti-CD37 immunoconjugate (e.g., Debio 1562) and the rituximab are administered intravenously (e.g., on the same day in separate compositions with the rituximab being administered after the anti-CD37 immunoconjugate (e.g., Debio 1562)).

In certain instances, after the anti-CD37 immunoconjugate is administered weekly in a 3-week cycle, the anti-CD37 immunoconjugate can be administered at a dose of 0.7 mg/kg once every three weeks. For example, the anti-CD37 immunoconjugate can be administered weekly in a single 3-week cycle and then administered at a dose of 0.7 mg/kg once every three weeks. The anti-CD37 immunoconjugate can be administered weekly in two consecutive 3-week cycles and then administered at a dose of 0.7 mg/kg once every three weeks. The anti-CD37 immunoconjugate can be administered weekly in three consecutive 3-week cycles and then administered at a dose of 0.7 mg/kg once every three weeks. The anti-CD37 immunoconjugate can be administered weekly in four consecutive 3-week cycles and then administered at a dose of 0.7 mg/kg once every three weeks. The anti-CD37 immunoconjugate can be administered weekly in five consecutive 3-week cycles and then administered at a dose of 0.7 mg/kg once every three weeks. The anti-CD37 immunoconjugate can be administered weekly in six consecutive 3-week cycles and then administered at a dose of 0.7 mg/kg once every three weeks. The anti-CD37 immunoconjugate can be administered weekly in seven consecutive 3-week cycles and then administered at a dose of 0.7 mg/kg once every three weeks. The anti-CD37 immunoconjugate can be administered weekly in eight consecutive 3-week cycles and then administered at a dose of 0.7 mg/kg once every three weeks. The anti-CD37 immunoconjugate can be administered weekly in nine consecutive 3-week cycles and then administered at a dose of 0.7 mg/kg once every three weeks. The anti-CD37 immunoconjugate can be administered weekly in ten consecutive 3-week cycles and then administered at a dose of 0.7 mg/kg once every three weeks. The anti-CD37 immunoconjugate can be administered weekly in eleven consecutive 3-week cycles and then administered at a dose of 0.7 mg/kg once every three weeks. The anti-CD37 immunoconjugate can be administered weekly in twelve consecutive 3-week cycles and then administered at a dose of 0.7 mg/kg once every three weeks.

The anti-CD37 immunoconjugate can be administered weekly in at least one 3-week cycles and then administered at a dose of 0.7 mg/kg once every three weeks. The anti-CD37 immunoconjugate can be administered weekly in at least two 3-week cycles and then administered at a dose of 0.7 mg/kg once every three weeks. The anti-CD37 immunoconjugate can be administered weekly in at least three 3-week cycles and then administered at a dose of 0.7 mg/kg once every three weeks. The anti-CD37 immunoconjugate can be administered weekly in at least four 3-week cycles and then administered at a dose of 0.7 mg/kg once every three weeks. The anti-CD37 immunoconjugate can be administered weekly in at least five 3-week cycles and then administered at a dose of 0.7 mg/kg once every three weeks. The anti-CD37 immunoconjugate can be administered weekly in at least six 3-week cycles and then administered at a dose of 0.7 mg/kg once every three weeks. The anti-CD37 immunoconjugate can be administered weekly in at least seven 3-week cycles and then administered at a dose of 0.7 mg/kg once every three weeks. The anti-CD37 immunoconjugate can be administered weekly in at least eight 3-week cycles and then administered at a dose of 0.7 mg/kg once every three weeks. The anti-CD37 immunoconjugate can be administered weekly in at least nine 3-week cycles and then administered at a dose of 0.7 mg/kg once every three weeks. The anti-CD37 immunoconjugate can be administered weekly in at least ten 3-week cycles and then administered at a dose of 0.7 mg/kg once every three weeks. The anti-CD37 immunoconjugate can be administered weekly in at least eleven 3-week cycles and then administered at a dose of 0.7 mg/kg once every three weeks. The anti-CD37 immunoconjugate can be administered weekly in at least twelve 3-week cycles and then administered at a dose of 0.7 mg/kg once every three weeks.

The anti-CD37 immunoconjugate can be administered weekly in one or more 3-week cycles until a favorable result (e.g., a complete response, a partial response, or stable disease) is observed and then administered at a dose of 0.7 mg/kg once every three weeks.

The present invention provides for methods of treating cancer in a human subject comprising administering a therapeutically effective amount of a CD37-binding agent to a subject (e.g., a subject in need of treatment). In certain embodiments, the cancer is a B-cell malignancy. In certain embodiments, the cancer is leukemia or lymphoma. In certain embodiments, the cancer is selected from the group consisting of B cell lymphomas, NHL, precursor B cell lymphoblastic leukemia/lymphoma and mature B cell neoplasms, B cell chronic lymphocytic leukemia (CLL)/small lymphocytic lymphoma (SLL), small cell lymphoma, B cell prolymphocytic leukemia, lymphoplasmacytic lymphoma, mantle cell lymphoma (MCL), follicular lymphoma (FL), low grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL). In certain embodiments, the cancer is selected from the group consisting of diffuse large B cell lymphoma (DLBCL), follicular lymphoma (FL), unspecified NHL, MALT lymphoma, mantle cell lymphoma (MCL), Burkitt's lymphoma (BL), and chronic lymphocytic leukemia (CLL). In certain embodiments, the cancer is relapsed or refractory NHL.

In certain instances, the cancer is a diffuse large B-cell lymphoma (DLBCL). The DLBCL can be a relapsed DLBCL. The DLBCL can be a refractory (i.e. not responding to or showing disease progression after first line of treatment) DLBCL. In certain instances, the DLBCL is not a refractory DLBCL.

In certain instances, administration of the anti-CD37 immunoconjugate, optionally in combination with an anti-CD20 therapy, increases progression-free survival (PFS), disease-free survival (DFS), duration of response (DOR), overall survival (OS), complete responses (CR), partial responses (PR), or, stable diseases (SD).

In certain instances, the human subject has received at least one prior treatment regimen for the cancer. In certain instances, the human subject has received no more than six prior treatment regimens for the cancer. In certain instances, the human subject has received at least one prior treatment, but no more than six prior treatment regimens for the cancer. In certain instances, the human subject has already received treatment with an anti-CD20 therapy. In certain instances, the anti-CD20 therapy included treatment with an anti-CD20 antibody, such as rituximab.

As provided herein, anti-CD37 immunoconjugates can be administered in a pharmaceutical composition. In certain instances, a pharmaceutical composition comprises anti-CD37 immunoconjugates (e.g., Debio 1562) and a pharmaceutically acceptable vehicle. Accordingly, provided herein are methods of administering pharmaceutical compositions comprising anti-CD37 immunoconjugates (e.g., Debio 1562) thereof having the desired degree of purity in a physiologically acceptable carrier, excipient, or stabilizer (Remington's Pharmaceutical Sciences (1990) Mack Publishing Co., Easton, PA). Acceptable carriers, excipients, or stabilizers are nontoxic to recipients at the dosages and concentrations employed. (See, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). The compositions to be used for in vivo administration can be sterile. This is readily accomplished by filtration through, e.g., sterile filtration membranes.

In certain instances, provided herein are methods of administering a pharmaceutical composition comprising anti-CD37 immunoconjugates (e.g., Debio 1562), wherein the anti-CD37 immunoconjugates in the pharmaceutical composition comprise 1-10 maytansinoids per antibody or antigen-binding fragment thereof. In certain instances, the anti-CD37 immunoconjugates in the pharmaceutical composition comprise 2-8 maytansinoids per antibody or antigen-binding fragment thereof.

In certain instances, provided herein are methods of administering a pharmaceutical composition comprising anti-CD37 immunoconjugates (e.g., Debio 1562), wherein the anti-CD37 immunoconjugates in the pharmaceutical composition comprise an average of 2-6 maytansinoids per antibody or antigen-binding fragment thereof. In certain instances, the anti-CD37 immunoconjugates in the pharmaceutical composition comprise an average of 2-5 maytansinoids per antibody or antigen-binding fragment thereof. In certain instances, the anti-CD37 immunoconjugates in the pharmaceutical composition comprise an average of 3-4 maytansinoids per antibody or antigen-binding fragment thereof. In certain instances, the anti-CD37 immunoconjugates in the pharmaceutical composition comprise an average of 3.5 maytansinoids per antibody or antigen-binding fragment thereof.

In certain instances, the methods further comprise administering a corticosteroid to the patient. In certain instances, the corticosteroid can be selected from the group consisting of prednisone, prednisolone, methylprednisolone, beclamethasone, betamethasone, dexamethasone, fludrocortisone, hydrocortisone, and triamcinolone. In certain instances, the corticosteroid can be dexamethasone. In certain instances, the corticosteroid can be administered as a pre-treatment, i.e., prior to the administration of the anti-CD37 immunoconjugates (e.g., Debio 1562). In certain instances, the corticosteroid can be administered during the administration of the anti-CD37 immunoconjugates (e.g., Debio 1562). In certain instances, the corticosteroid can be administered during the administration of the anti-CD37 immunoconjugates (e.g., Debio 1562) and at least one additional time from about one day after to about five days after the administration of the anti-CD37 immunoconjugates (e.g., Debio 1562). In certain instances, the corticosteroid can be administered during the administration of the anti-CD37 immunoconjugates (e.g., Debio 1562) and at least one additional time from about one day after to about four days after the administration of the anti-CD37 immunoconjugates (e.g., Debio 1562). In certain instances, the corticosteroid can be administered during the administration of the anti-CD37 immunoconjugates (e.g., Debio 1562) and at least one additional time from about one day after to about three days after the administration of the anti-CD37 immunoconjugates (e.g., Debio 1562). In certain instances, the corticosteroid can be administered during the administration of the anti-CD37 immunoconjugate (e.g., Debio 1562) and at least one additional time from about one day after to about two days after the administration of the anti-CD37 immunoconjugate (e.g., Debio 1562). In certain instances, the corticosteroid can be administered during the administration of the anti-CD37 immunoconjugate (e.g., Debio 1562) and at least one additional time from about two days after to about five days after the administration of the anti-CD37 immunoconjugate (e.g., Debio 1562). In certain instances, the corticosteroid can be administered during the administration of the anti-CD37 immunoconjugate (e.g., Debio 1562) and at least one additional time from about two days after to about four days after the administration of the anti-CD37 immunoconjugate (e.g., Debio 1562). In certain instances, the corticosteroid can be administered during the administration of the anti-CD37 immunoconjugate (e.g., Debio 1562) and at least one additional time from about two days after to about three days after the administration of the anti-CD37 immunoconjugate (e.g., Debio 1562). In certain instances, the corticosteroid can be administered during the administration of the anti-CD37 immunoconjugate (e.g., Debio 1562) and at about two days after and at about three days after the administration of the anti-CD37 immunoconjugate (e.g., Debio 1562). In certain instances, the corticosteroid can be administered during the administration of the anti-CD37 immunoconjugate (e.g., Debio 1562) and at about two days after and at about three days after the administration of the anti-CD37 immunoconjugate (e.g., Debio 1562). In certain instances, the corticosteroid can be administered by peri-infusion. In certain instances, the corticosteroid is administered 30 to 60 minutes prior to administration of the anti-CD37 immunoconjugate (e.g., Debio 1562). In certain instances, the corticosteroid is administered 30 to 60 minutes prior to administration of the anti-CD37 immunoconjugate (e.g., Debio 1562) and on at least one additional time on days 1 to 3 following administration of the anti-CD37 immunoconjugate (e.g., Debio 1562). Pre-infusion intravenous steroid administration was found to eliminate hematological adverse effects. In certain instances, the corticosteroid is administered on at least one of days 2 and 3 following infusion.

In certain instances the corticosteroid is administered by IV. In certain instances, the steroid is administered orally.

In certain instances, the corticosteroid is administered intravenously 30 to 60 minutes prior to the administration of the anti-CD37 immunoconjugate (e.g., Debio 1562) and the corticosteroid is administered orally on days 2 and 3 of a 3-week anti-CD37 immunoconjugate administration cycle.

In certain instances, the corticosteroid to be administered can be dexamethasone. In certain instances, the corticosteroid to be administered can be methylprednisolone. In certain instances, the corticosteroid to be administered can be prednisolone.

In certain instances, from about 5 mg to about 10 mg dexamethasone is administered. In certain instances, from about 8 mg to about 10 mg dexamethasone is administered. In certain instances, about 10 mg dexamethasone is administered. In certain instances, about 8 mg dexamethasone is administered. In certain instances about 10 mg dexamethasone is administered by IV 30 to 60 minutes prior to administration of the anti-CD37 immunoconjugate (e.g., Debio 1562). In certain instances about 10 mg dexamethasone is administered by IV at the time of administration of the anti-CD37 immunoconjugate (e.g., Debio 1562) and again about 1 to about 5 days after administration of the anti-CD37 immunoconjugate (e.g., Debio 1562). In certain instances, the corticosteroid is administered by IV 30 to 60 minutes prior to administration of the anti-CD37 immunoconjugate (e.g., Debio 1562) and one dose of 8 mg of dexamethasone is delivered orally on days 2 and 3 following infusion.

In certain instances, 10 mg dexamethasone is administered intravenously 30 to 60 minutes prior to the administration of the anti-CD37 immunoconjugate (e.g., Debio 1562) and 8 mg dexamethasone is administered orally on days 2 and 3 of a 3-week anti-CD37 immunoconjugate administration cycle.

In certain instances, the methods further comprise administering a growth factor to the patient. Methods of administering white blood cell growth factors are reviewed, for example, in Smith et al., *J. Clin. Oncol.* 24: 3187-3205 (2006), which is herein incorporated by reference in its entirety. Growth factor treatment may decrease the likelihood of neutropenias. In certain instances, the growth factor can be granulocyte colony-stimulating factor (G-CSF). In certain instances, the growth factor can be granulocyte-macrophage colony-stimulating factor (GM-CSF). In certain instances, the growth factor can be macrophage colony-stimulating factor (M-CSF). In certain instances, the growth factor can be filgrastim. In certain instances, the growth factor can be pegylated, e.g., pegylated G-CSF. In certain instances, the growth factor can be pegfilgrastim, marketed as Neulasta®.

In certain instances, the growth factor can be administered as a pre-treatment, i.e., prior to the administration of the anti-CD37 immunoconjugate (e.g., Debio 1562). In certain instances, the anti-CD37 immunoconjugate (e.g., Debio 1562) is administered on a 3-week (about 21-day) cycle and the growth factor can be administered at any point during the 3-week (about 21-day) cycle. In certain instances, the anti-CD37 immunoconjugate (e.g., Debio 1562) is administered on a 3-week (about 21-day) cycle and the growth factor can be administered early to middle cycle of the 3-week (about 21-day) cycle. In certain instances, the growth factor can be administered on at least one day from day 1 to about day 21 of the 3-week (about 21-day) cycle. In certain instances, the growth factor can be administered on at least one day from day 1 to about day 20 of the 3-week (about 21-day) cycle. In certain instances, the growth factor can be administered on at least one day from day 1 to about day 19 of the 3-week (about 21-day) cycle. In certain instances, the growth factor can be administered on at least one day from day 1 to about day 18 of the 3-week (about 21-day) cycle. In certain instances, the growth factor can be administered on at least one day from day 1 to about day 17 of the 3-week (about 21-day) cycle. In certain instances, the growth factor can be administered on at least one day from day 1 to about day 16 of the 3-week (about 21-day) cycle. In certain instances, the growth factor can be administered on at least one day from day 1 to about day 14 of the 3-week (about 21-day) cycle. In certain instances, the growth factor can be administered on at least one day from day 1 to about day 12 of the 3-week (about 21-day) cycle. In certain instances, the growth factor can be administered on at least one day from day about 15 to about day 21 of the 3-week (about 21-day) cycle. In certain instances, the growth factor can be administered on at least one day from about day 3 to about day 10 of the 3-week (about 21-day) cycle. In certain instances, the growth factor can be administered at least twice from about day 3 to about day 10 of the 3-week (about 21-day) cycle. In certain instances, the growth factor can be administered at least three times from about day 3 to about day 10 of the 3-week (about 21-day) cycle. In certain instances, the growth factor can be administered on at least one day from about day 4 to about day 10 of the 3-week (about 21-day) cycle. In certain instances, the growth factor can be administered on at least one day from day 5 to day 8 of the 3-week (about 21-day) cycle. In certain instances, the growth factor can be administered on at least one day selected from day 5, day 6, and day 8 of the 3-week (about 21-day) cycle. In certain instances, the growth factor can be administered on days 5, 6, and 8 of the 3-week (about 21-day) cycle.

In certain instances, G-CSF is administered at a dose of about 1 µg/kg body weight to about 15 µg/kg body weight, per day that the growth factor is administered. In certain instances, G-CSF is administered at a dose of about 5 µg/kg/day. In certain instances, G-CSF is administered at a dose of about 10 µg/kg/day.

In certain instances, G-CSF is administered at a dose of about 200 µg to about 600 µg per day. In certain instances, G-CSF is administered at a dose of about 300 µg to about 500 µg per day. In certain instances, G-CSF is administered at a dose of about 300 µg to about 480 µg per day. In certain instances, G-CSF is administered at a dose of about 300 µg/day. In certain instances, G-CSF is administered at a dose of about 400 µg/day. In certain instances, G-CSF is administered at a dose of about 480 µg/day. In certain instances, G-CSF is administered at a dose of about 500 µg/day.

In certain instances, GM-CSF is administered at a dose of about 100 µg/m² to about 500 µg/m², per day that the growth factor is administered. In certain instances, GM-CSF is administered at a dose of about 250 µg/m²/day.

In certain instances, GM-CSF is administered at a dose of about 200 µg to about 600 µg per day. In certain instances, GM-CSF is administered at a dose of about 300 µg to about 500 µg per day. In certain instances, GM-CSF is administered at a dose of about 300 µg to about 480 µg per day. In certain instances, GM-CSF is administered at a dose of about 300 µg/day. In certain instances, G-CSF is administered at a dose of about 400 µg/day. In certain instances, GM-CSF is administered at a dose of about 480 µg/day. In certain instances, GM-CSF is administered at a dose of about 500 µg/day.

In certain instances, pegfilgrastim is administered at a dose of about 6 mg per cycle. In certain instances, pegfilgrastim is administered at a dose of about 10 µg/kg to about 500 µg/kg per cycle. In certain instances, pegfilgrastim is administered at a dose of about 10 µg/kg to about 400 µg/kg per cycle. In certain instances, pegfilgrastim is administered at a dose of about 50 µg/kg to about 300 µg/kg per cycle. In certain instances, pegfilgrastim is administered at a dose of about 50 µg/kg to about 200 µg/kg per cycle. In certain instances, pegfilgrastim is administered at a dose of about 50 µg/kg to about 150 µg/kg per cycle. In certain instances, pegfilgrastim is administered at a dose of about 100 µg/kg per cycle.

In certain instances, administration of corticosteroids and/or G-CSF to the dosing protocol allows a higher dose to be administered. In certain instances, patients stay on the treatment longer due to the administration of corticosteroids and/or G-CSF. In certain instances, less neutropenia is observed due to the administration of corticosteroids and/or G-CSF. In certain instances, more clinical benefits are observed due to the administration of corticosteroids and/or G-CSF.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1: Design of a Weekly Dosing Schedule

A weekly dosing schedule of Debio 1562 was designed to improve the safety profile and optimize the duration of tumor exposure to Debio 1562 in order to enhance efficacy.

Based on all the pharmacokinetics (PK), pharmacodynamics (PD) and safety data gathered in previous studies, a modeling algorithm was designed that allows dosing schedule simulations. Simulation of Debio 1562 drug concentrations in patients at various weekly dosing schedules as compared to administration every three weeks are shown in FIGS. 1-5. Each scenario was simulated 1000 times, and simulations were summarized as mean and 90% prediction intervals. Simulations were performed for 6 treatment cycles. Compared with the 3-weekly schedule, the simulations show that these weekly dosing schedules of Debio 1562 should prolong exposure of CD37 receptors to Debio 1562 over each three-week cycle and decrease the $C_{max}$ (if $C_{max}$ is too high, it may be associated with toxicities).

As an example of such weekly dosage regimen, 0.4/0.2/0.2 mg/kg, on week 1, 2, and 3 of each cycle respectively (cumulative 0.8 mg/kg over three weeks) would be expected to optimize the benefit-risk of Debio 1562 for DLBCL patients.

With regard to safety, the total dose over three weeks would not exceed 1 mg/kg, which was previously determined as the maximum tolerated dose (MTD) for Debio 1562 (without G-CSF) in Phase 1. It is also worth noting that the majority of patients experienced no decrease in neutrophil count during single Q3W dosing with 0.2-0.4 mg/kg dose in the Phase 1 study. As such, a more frequent QW dosing schedule with 0.4/0.2/0.2 mg/kg (combined with rituximab Q3W at 375 mg/m$^2$) should not increase the risk of neutropenia.

With regard to efficacy: in the monotherapy Phase 1 study, "theoretical" Receptor Occupancy (RO) values derived from observed $C_{max}$ showed that even at low dose levels, a saturation of >>95% of the CD37 sites was expected (between 96.2% and 99.9% on average). Therefore, a 0.4 mg/kg loading dose followed by 2 weekly doses of 0.2 mg/kg is expected to provide adequate target saturation across a 3-weeks cycle.

As such, more frequent dosing is expected to prolong the synergistic effect and effector-mediated activities of Debio 1562 combined with 3-weekly (Q3W) dosing of rituximab at 375 mg/m$^2$, resulting in improved efficacy.

Example 2: Study of Debio 1562 (QW) in Combination with Rituximab in Patients with Relapsed or Refractory DLBCL A Phase 2 clinical trial was initiated and is being conducted including the weekly Debio 1562 dosing schedule developed in Example 1 (in combination with Q3W rituximab at 375 mg/m$^2$) to confirm the efficacy and tolerability of Debio 1562 in combination with rituximab in patients with relapsed and/or refractory diffuse large B-cell lymphoma (DLBCL) and other forms of Non-Hodgkin's Lymphoma (NCT 02564744). The trial includes 3 parts. Part 1 is a safety run-in in which about 15 patients with a diagnosis of R/R DLBCL, Follicular Lymphoma (FL), Marginal Zone Lymphoma/Mucosa-associated lymphoid tissue (MZL/MALT), Mantle Cell Lymphoma (MCL) or other NHL subtypes with the Sponsor's approval are enrolled. Part 2 is an initial assessment of safety and efficacy of administering Debio 1562 once every three weeks (Q3W) and once every week (QW). About 30 patients with a diagnosis of relapsed DLBCL are enrolled. Part 3 is an expansion phase in which about 30 additional patients with a diagnosis of relapsed DLBCL are enrolled.

Study Design

In Part 1, the safety run-in, patients with DLBCL, FL, MCL, MZL/MALT or other NHL subtypes participate. At least six DLBCL and six FL NHL patients are enrolled. Patients are given Debio 1562 and rituximab on the same day (i.e., Day 1) once every three weeks (Q3W) intravenously (IV). Debio 1562 is given at a dose of 0.7 mg/kg, followed by 375 mg/m$^2$ of rituximab. Following review of safety and PK data, the Q3W dosing schedule will continue with the 0.7 mg/kg dose of IMGN or an alternate higher (1.0 mg/kg) or lower dose of Debio 1562.

In Part 2, the initial assessment of safety and efficacy of Q3W and QW dosing regimens, patients with relapsed DLBCL are enrolled into two parallel cohorts according to the dosing regimen of Debio 1562: cohort A (21-day treatment cycle with a Q3W dosing schedule) and cohort B (21-day treatment cycle with a once weekly [QW] dosing schedule). Patients in cohort A receive Debio 1562 and rituximab IV on the same day (Day 1) on a Q3W dosing schedule. Debio 1562 is given at a dose of 0.7 mg/kg (followed by 375 mg/m$^2$ of rituximab). Cohort B receives a QW dosing schedule of Debio 1562: 0.4, 0.2, and 0.2 mg/kg of Debio 1562 is administered IV to patients on Day 1, Day 8 and Day 15 of a 21-day treatment cycle, respectively. Rituximab is administered IV at a dose of 375 mg/m$^2$ on Day 1 of each treatment cycle (following IMGN529). Patients in both cohorts will be treated for a maximum of six 21-day cycles.

In Part 3, the expansion, additional relapsed DLBCL patients are enrolled. Patients are treated with six 21-day cycles of Q3W and/or QW Debio 1562 along with rituximab.

In all parts, anti-tumor activity is assessed by the Lugano Classification.

In all parts, patients receive steroid prophylaxis. Prior to receiving Debio 1562 and rituximab, patients are given dexamethasone IV at 8 mg (or equivalent), acetaminophen PO or IV 325-650 mg, and an antihistamine (e.g. 25-50 mg diphenhydramine or equivalent) approximately 30-60 minutes prior to the Debio 1562 infusion. Patients are also instructed to take oral dexamethasone at 8 mg/day on Days 2 and 3, following the infusion. If needed, patients are also treated with granulocyte colony-stimulating factor support to mitigate neutropenia.

Patients

Adult (≥18 years) patients have histopathologically confirmed relapsed and/or refractory DLBCL, FL, MZL/MALT, MCL, or other NHL subtypes according to the World Health Organization (WHO) classification 2008. Patients have received no more than six prior treatment regimens and have an evaluable or measurable disease in accordance with the International Working Group Guidelines for Lymphoma. Patients have an ECOG Performance Status of 0-2.

For Part 2 and Part 3 of the study, patients have histopathologically and clinically confirmed diagnosis of relapsed DLBCL. Patients are considered to have a relapsed disease if they show a duration of response of at least 24 weeks after their first line of therapy.

No patients have CLL or SLL. No patients received prior anti-CD36 therapy or anti-CD20 monoclonal antibody therapy within 14 days of participation.

Safety and Pharmacokinetic Evaluation

Adverse events are monitored continuously throughout the study. Adverse events include any noxious, pathologic, or unintended change in anatomical, physiologic, or metabolic function as indicated by physical signs, symptoms, or laboratory changes occurring in any phase of a clinical study, whether or not considered study drug-related. PK parameters that are evaluated include, but are not limited to: $C_{max}$, $T_{max}$, Terminal half-life ($t_{1/2}$), $V_{ss}$, CL, $AUC_{0-t}$, $AUC_{inf}$. These will be derived from plasma concentrations of Debio 1562, total and/or naked humanized CD37 antibody (huCD37-3), DM1 (free and bound), as well as potential catabolites, and total rituximab.

Efficacy Evaluation

The best Overall Response (OR) is determined for each evaluable patient as CR, PR, stable disease (SD), or relapsed disease/PD. The overall response rate (ORR) is tabulated by dose cohort as well as the dose at which the response occurred along with the 95% confidence interval (CI). To meet the definition of response-evaluable, patients must have undergone radiographic assessment at baseline, received at least one dose of Debio 1562 and rituximab, and must have had at least one post-dose tumor assessment. Overall survival (OS) at one year is analyzed using the Kaplan-Meier method. Median OS and 95% CI (if feasible). The duration of response (DoR) is estimated for all evaluable patients who achieve an objective response (PR or CR). Progression free survival (PFS) at six months and one year are analyzed using the Kaplan-Meier method.

The exposure, $C_{max}$, efficacy and safety of the QW dosing schedule are compared to the Q3W schedule.

Example 3: Study of Debio 1562 Pharmacokinetics and Pharmacodynamics in Q3W and QW Dosing Regimens The pharmacokinetics and pharmacodynamics studies were conducted with subjects from Cohorts A and B in Example 2. Blood was taken at several time points during the cycle and used for pharmacokinetic measurements.

The preliminary results revealed that the rate of exposure ($C_{max}$) is approximately dose proportional between the Q3W dosing regimen and the QW dosing regimen (FIG. 6). Surprisingly though, the extent of exposure over a three-week cycle in the plasma as characterized by the area under the curve (AUC) for the QW dosing regimen was similar to that of the Q3W dosing regimen (FIG. 6). This was surprising because, even if the total dose administered over three weeks is approximatively the same (0.7 mg/kg for Q3W vs. 0.4+0.2+0.2=0.8 mg/kg for QW), previous reports found that clearance of Debio 1562 was substantially higher at low doses such as 0.4 mg/kg and 0.2 mg/kg, and the half-life was lower (see Stathis et al., *Invest New Drugs* 36: 869-876 (2018)). Nonetheless, the administration of such lower doses as per the Cohort B schedule did not result in a substantial decrease in exposure (AUC). In addition, the $C_{last}$ (last Debio 1562 concentration measured during a cycle before the next Debio 1562 administration) revealed that the QW dosing regimen allowed to maintain a higher Debio 1562 concentration throughout the 3-week cycle than the Q3W dosing regimen (FIG. 6).

This data demonstrated that fractionating the once every 3 week dose into three weekly doses had an exposure benefit. Although the extent of exposure (AUC) is maintained in both dosing regimens, the higher $C_{last}$ in the QW regimen indicates that the QW dosing regimen maintains a higher average concentration pressure on tumor cells throughout the 3-week cycle. This is expected to improve the efficacy of Debio 1562, e.g., when combined with an anti-CD20 therapy. Moreover, the $C_{max}$ was lower in the QW regimen than the Q3W regimen, indicating that the QW administration would not increase the risk of adverse effects.

The receptor occupancy (RO) of Debio 1562 was measured on CD19+B, CD3+T, and CD56+NK cells on samples obtained from subjects in Cohort A and B. Because of the rapid depletion of B cells, RO evaluation of this specific lymphocyte population was not possible. In Cohorts A and B, greater than 80% of the CD37 molecule expressed on CD3+T and CD56+NK lymphocyte populations are rapidly C1D1 (cycle 1-dose 1) occupied by Debio 1562 after administration. The maximum RO observed at C1D2 (cycle 1-dose 2) and C1D3 was greater than 90% for both cohorts. No RO was observed in samples collected just before the re-administration of Debio 1562 in cycle 2 and cycle 3 in the patients analyzed. Thus, a rapid (C1D1) and complete (>80%) RO was observed in both cohorts without any obvious differences between them. FIG. 7 shows the preliminary individual RO measurement at cycles 1, 2, and 3 in CD3+ cells.

The pharmacokinetic and RO data suggest that fractionating the Q3W dose into weekly administrations (QW) would not jeopardize either the exposure or the target attainment. A weekly administration would maintain "exposure pressure" on CD37-bearing cells during the 3-week cycle, e.g., when combined with rituximab.

Pharmacokinetic exposure was also compared in patients with varying responses to Debio 1562 (FIG. 8). The preliminary response rate appeared to be higher in the QW regimen. Exposure (AUC) in the complete responders (CR) of the QW regimen was higher than in the CRs of the Q3W regimen. In parallel, safety was comparable in the QW regimen and the Q3W regimen.

In sum, these results demonstrate that fractionated administration of Debio 1562 once weekly in a three-week cycle results in a lower rate of exposure ($C_{max}$), a similar extent of exposure (AUC), and an increased concentration pressure on tumor cells ($C_{last}$) per three-week cycle as compared to administration once every three weeks.

It is to be appreciated that the Detailed Description section, and not the Summary and Abstract sections, is intended to be used to interpret the claims. The Summary and Abstract sections sets forth one or more, but not all, exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for treating a cancer in a human patient comprising administering to the patient a pharmaceutical composition comprising an anti-CD37 immunoconjugate once a week in a three-week cycle, wherein:
   a) 0.4 mg/kg of the immunoconjugate are administered in the first week, 0.2 mg/kg are administered in the second week, and 0.2 mg/kg are administered in the third week;
   b) 0.2 mg/kg of the immunoconjugate are administered in the first week, 0.2 mg/kg are administered in the second week, and 0.2 mg/kg are administered in the third week;
   c) 0.3 mg/kg of the immunoconjugate are administered in the first week, 0.3 mg/kg are administered in the second week, and 0.3 mg/kg are administered in the third week;
   d) 0.3 mg/kg of the immunoconjugate are administered in the first week, 0.3 mg/kg are administered in the second week, and 0.2 mg/kg are administered in the third week;
   e) 0.3 mg/kg of the immunoconjugate are administered in the first week, 0.2 mg/kg are administered in the second week, and 0.2 mg/kg are administered in the third week;
   f) 0.4 mg/kg of the immunoconjugate are administered in the first week, 0.3 mg/kg are administered in the second week, and 0.3 mg/kg are administered in the third week;
   g) 0.4 mg/kg of the immunoconjugate are administered in the first week, 0.3 mg/kg are administered in the second week, and 0.2 mg/kg are administered in the third week;
   h) 0.5 mg/kg of the immunoconjugate are administered in the first week, 0.3 mg/kg is administered in the second week, and 0.2 mg/kg are administered in the third week;
   i) 0.5 mg/kg of the immunoconjugate are administered in the first week, 0.2 mg/kg are administered in the second week, and 0.2 mg/kg are administered in the third week; or
   j) 0.6 mg/kg of the immunoconjugate are administered in the first week, 0.2 mg/kg are administered in the second week, and 0.2 mg/kg are administered in the third week;
   wherein the immunoconjugate comprises (i) an antibody or antigen-binding fragment thereof comprising a VH-CDR1 comprising the amino acid sequence of SEQ ID NO:2, a VH-CDR2 comprising the amino acid sequence of SEQ ID NO:3, a VH-CDR3 comprising the amino acid sequence of SEQ ID NO:4, a VL-CDR1 comprising the amino acid sequence of SEQ ID NO:5, a VL-CDR2 comprising the amino acid sequence of SEQ ID NO:6, and a VL-CDR3 comprising the amino acid sequence of SEQ ID NO:7 and (ii) a maytansinoid.

2. The method of claim 1, wherein the antibody or antigen-binding fragment comprises a variable heavy chain comprising the amino acid sequence of SEQ ID NO:8 and a variable light chain comprising the amino acid sequence of SEQ ID NO:10.

3. The method of claim 1, wherein the maytansinoid is DM1.

4. The method of claim 1, wherein the maytansinoid is linked to the antibody or antigen-binding fragment by an SMCC linker.

5. The method of claim 1, wherein the antibody comprises a full-length heavy chain comprising the amino acid sequence of SEQ ID NO: 11 and a full-length light chain comprising the amino acid sequence of SEQ ID NO: 12, wherein the maytansinoid is DM1, and wherein the DM1 is linked to the antibody by an SMCC linker.

6. The method of claim 1, wherein the pharmaceutical composition comprises at least two of the immunoconjugates and the immunoconjugates comprise an average of 3 to 4 maytansinoids per antibody.

7. The method of claim 1, wherein the immunoconjugate is administered for six three-week cycles.

8. The method of claim 1, wherein the pharmaceutical composition comprises at least two of the immunoconjugates and the immunoconjugates comprise an average of 3 to 4 maytansinoids per antibody wherein the antibody comprises a full-length heavy chain comprising the amino acid sequence of SEQ ID NO: 11 and a full-length light chain comprising the amino acid sequence of SEQ ID NO:12, wherein the maytansinoid is DM1, and wherein the DM1 is linked to the antibody by an SMCC linker, wherein the immunoconjugate is administered in combination with 375 mg/m$^2$ of rituximab administered once every three weeks on day one of the three-week cycle after administration of the immunoconjugate.

9. The method of claim 1, further comprising administering a corticosteroid to the patient and/or a growth factor to the patient.

10. The method of claim 1, wherein the cancer is a B cell malignancy.

11. The method of claim 1, wherein the cancer is leukemia or lymphoma.

12. The method of claim 1, wherein the cancer is diffuse large B-cell lymphoma (DLBCL).

13. The method of claim 1, wherein the cancer is selected from the group consisting of relapsed and/or refractory DLBCL, Follicular Lymphoma (FL), Marginal Zone Lymphoma/Mucosa-associated lymphoid tissue (MZL/MALT), or Mantle Cell Lymphoma (MCL).

14. The method of claim 1, wherein the cancer is selected from the group consisting of precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma, plasmacytoma, plasma cell myeloma, post-transplant lymphoproliferative disorder, Waldenstrom's macroglobulinemia, and anaplastic large-cell lymphoma (ALCL).

15. The method of claim 1, wherein the anti-CD37 immunoconjugate is administered once a week in a three-week cycle for at least one, at least two, at least three, at least four, at least five, at least six, at least seven, at least eight, at least nine, at least ten, at least eleven, or at least twelve three-week cycles.

16. The method of claim 15, comprising administering the anti-CD37 immunoconjugate at a dose of 0.7 mg/kg once every three weeks after the at least one, at least two, at least three, at least four, at least five, at least six, at least seven, at least eight, at least nine, at least ten, at least eleven or at least twelve three-week cycles of weekly administration.

17. A method for treating a cancer in a human patient comprising administering to the patient a pharmaceutical composition comprising an anti-CD37 immunoconjugate once a week in a three-week cycle, wherein:

a) 0.4 mg/kg of the immunoconjugate are administered in the first week, 0.2 mg/kg are administered in the second week, and 0.2 mg/kg are administered in the third week;
b) 0.2 mg/kg of the immunoconjugate are administered in the first week, 0.2 mg/kg are administered in the second week, and 0.2 mg/kg are administered in the third week;
c) 0.3 mg/kg of the immunoconjugate are administered in the first week, 0.3 mg/kg are administered in the second week, and 0.3 mg/kg are administered in the third week;
d) 0.3 mg/kg of the immunoconjugate are administered in the first week, 0.3 mg/kg are administered in the second week, and 0.2 mg/kg are administered in the third week;
e) 0.3 mg/kg of the immunoconjugate are administered in the first week, 0.2 mg/kg are administered in the second week, and 0.2 mg/kg are administered in the third week;
f) 0.4 mg/kg of the immunoconjugate are administered in the first week, 0.3 mg/kg are administered in the second week, and 0.3 mg/kg are administered in the third week;
g) 0.4 mg/kg of the immunoconjugate are administered in the first week, 0.3 mg/kg are administered in the second week, and 0.2 mg/kg are administered in the third week;
h) 0.5 mg/kg of the immunoconjugate are administered in the first week, 0.3 mg/kg is administered in the second week, and 0.2 mg/kg are administered in the third week;
i) 0.5 mg/kg of the immunoconjugate are administered in the first week, 0.2 mg/kg are administered in the second week, and 0.2 mg/kg are administered in the third week; or
j) 0.6 mg/kg of the immunoconjugate are administered in the first week, 0.2 mg/kg are administered in the second week, and 0.2 mg/kg are administered in the third week;

wherein the immunoconjugate comprises (i) an antibody or antigen-binding fragment thereof comprising a VH-CDR1 comprising the amino acid sequence of SEQ ID NO:2, a VH-CDR2 comprising the amino acid sequence of SEQ ID NO:3, a VH-CDR3 comprising the amino acid sequence of SEQ ID NO:4, a VL-CDR1 comprising the amino acid sequence of SEQ ID NO:5, a VL-CDR2 comprising the amino acid sequence of SEQ ID NO:6, and a VL-CDR3 comprising the amino acid sequence of SEQ ID NO:7 and (ii) a maytansinoid, wherein the immunoconjugate is administered in combination with an anti-CD20 therapy.

18. The method of claim 17, wherein the anti-CD20 therapy is rituximab.

19. The method of claim 18, wherein 375 mg/m$^2$ of the rituximab is administered once every three weeks.

20. The method of claim 17, wherein the anti-CD20 therapy is an antigen-binding fragment of rituximab or a biosimilar of rituximab, ofatumumab, obinutuzumab, veltuzumab, an antigen-binding fragment of ofatumumab, obinutuzumab, or veltuzumab, or a biosimilar of ofatumumab, obinutuzumab, or veltuzumab.

* * * * *

```
                         SEQUENCE LISTING

<160> NUMBER OF SEQ ID NOS: 14

<210> SEQ ID NO 1
<211> LENGTH: 280
<212> TYPE: PRT
<213> ORGANISM: Artificial Sequence
<220> FEATURE:
<223> OTHER INFORMATION: human CD37

<400> SEQUENCE: 1

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Tyr Arg
        275                 280

<210> SEQ ID NO 2
```

```
<211> LENGTH: 5
<212> TYPE: PRT
<213> ORGANISM: Artificial Sequence
<220> FEATURE:
<223> OTHER INFORMATION: VH-CDR1

<400> SEQUENCE: 2

Thr Ser Gly Val Ser
1               5

<210> SEQ ID NO 3
<211> LENGTH: 9
<212> TYPE: PRT
<213> ORGANISM: Artificial Sequence
<220> FEATURE:
<223> OTHER INFORMATION: VH-CDR2

<400> SEQUENCE: 3

Val Ile Trp Gly Asp Gly Ser Thr Asn
1               5

<210> SEQ ID NO 4
<211> LENGTH: 7
<212> TYPE: PRT
<213> ORGANISM: Artificial Sequence
<220> FEATURE:
<223> OTHER INFORMATION: VH-CDR3

<400> SEQUENCE: 4

Gly Gly Tyr Ser Leu Ala His
1               5

<210> SEQ ID NO 5
<211> LENGTH: 11
<212> TYPE: PRT
<213> ORGANISM: Artificial Sequence
<220> FEATURE:
<223> OTHER INFORMATION: VL-CDR1

<400> SEQUENCE: 5

Arg Ala Ser Glu Asn Ile Arg Ser Asn Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: VL-CDR2

<400> SEQUENCE: 6

Val Ala Thr Asn Leu Ala Asp
1               5

<210> SEQ ID NO 7
<211> LENGTH: 9
<212> TYPE: PRT
<213> ORGANISM: Artificial Sequence
<220> FEATURE:
<223> OTHER INFORMATION: VL-CDR3

<400> SEQUENCE: 7

Gln His Tyr Trp Gly Thr Thr Trp Thr
1               5

<210> SEQ ID NO 8
<211> LENGTH: 115
```

```
<212> TYPE: PRT
<213> ORGANISM: Artificial Sequence
<220> FEATURE:
<223> OTHER INFORMATION: huCD37-3 VH (version 1.0)

<400> SEQUENCE: 8

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser
        115

<210> SEQ ID NO 9
<211> LENGTH: 115
<212> TYPE: PRT
<213> ORGANISM: Artificial Sequence
<220> FEATURE:
<223> OTHER INFORMATION: huCD37-3 VH (version 1.1)

<400> SEQUENCE: 9

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser
        115

<210> SEQ ID NO 10
<211> LENGTH: 108
<212> TYPE: PRT
<213> ORGANISM: Artificial Sequence
<220> FEATURE:
<223> OTHER INFORMATION: huCD37-3 VL

<400> SEQUENCE: 10

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
```

```
                20                  25                  30
Leu Ala Trp Tyr Gln Gln Lys Pro Gly Lys Ser Pro Lys Leu Leu Val
            35                  40                  45

Asn Val Ala Thr Asn Leu Ala Asp Gly Val Pro Ser Arg Phe Ser Gly
        50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg
                100                 105

<210> SEQ ID NO 11
<211> LENGTH: 444
<212> TYPE: PRT
<213> ORGANISM: Artificial Sequence
<220> FEATURE:
<223> OTHER INFORMATION: huCD37-3 FL HC (version 1.0)

<400> SEQUENCE: 11

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
```

```
            275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
            435                 440
```

<210> SEQ ID NO 12
<211> LENGTH: 214
<212> TYPE: PRT
<213> ORGANISM: Artificial Sequence
<220> FEATURE:
<223> OTHER INFORMATION: huCD37-3 FL LC

<400> SEQUENCE: 12

```
Asp Ile Gln Met Thr Gln Ser Pro Ser Ser Leu Ser Val Ser Val Gly
1               5                   10                  15
Glu Arg Val Thr Ile Thr Cys Arg Ala Ser Glu Asn Ile Arg Ser Asn
                20                  25                  30
Leu Ala Trp Tyr Gln Gln Lys Pro Gly Lys Ser Pro Lys Leu Leu Val
            35                  40                  45
Asn Val Ala Thr Asn Leu Ala Asp Gly Val Pro Ser Arg Phe Ser Gly
        50                  55                  60
Ser Gly Ser Gly Thr Asp Tyr Ser Leu Lys Ile Asn Ser Leu Gln Pro
65                  70                  75                  80
Glu Asp Phe Gly Thr Tyr Tyr Cys Gln His Tyr Trp Gly Thr Thr Trp
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
```

Phe Asn Arg Gly Glu Cys
    210

<210> SEQ ID NO 13
<211> LENGTH: 121
<212> TYPE: PRT
<213> ORGANISM: Artificial Sequence
<220> FEATURE:
<223> OTHER INFORMATION: Rituximab variable heavy chain

<400> SEQUENCE: 13

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 14
<211> LENGTH: 106
<212> TYPE: PRT
<213> ORGANISM: Artificial Sequence
<220> FEATURE:
<223> OTHER INFORMATION: Rituximab variable light chain

<400> SEQUENCE: 14

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105